(12) United States Patent
Gowey

(10) Patent No.: US 10,744,151 B1
(45) Date of Patent: Aug. 18, 2020

(54) MICRO-RNA PROFILING, COMPOSITIONS, AND METHODS OF TREATING DISEASES

(71) Applicant: GOWEY RESEARCH GROUP, PLLC, Flagstaff, AZ (US)

(72) Inventor: Brandie Gowey, Flagstaff, AZ (US)

(73) Assignee: GOWEY RESEARCH GROUP PLLC, Flagstaff, AZ (US)

( * ) Notice: Subject to any disclaimer, the term of this patent is extended or adjusted under 35 U.S.C. 154(b) by 0 days.

(21) Appl. No.: 16/153,342

(22) Filed: Oct. 5, 2018

Related U.S. Application Data

(63) Continuation-in-part of application No. 15/791,147, filed on Oct. 23, 2017, now abandoned, which is a continuation-in-part of application No. 15/420,374, filed on Jan. 31, 2017, now abandoned, which is a continuation-in-part of application No. 14/990,107, filed on Jan. 7, 2016, which is a continuation-in-part of application No. 14/306,581, filed on Jun. 17, 2014, now abandoned, which is a continuation-in-part of application No. 14/305,933, filed on Jun. 16, 2014, now abandoned, which is a continuation-in-part of application No. 13/309,144, filed on Dec. 1, 2011, now abandoned.

(60) Provisional application No. 62/411,439, filed on Oct. 21, 2016, provisional application No. 61/835,749, filed on Jun. 17, 2013, provisional application No. 61/835,741, filed on Jun. 17, 2013, provisional application No. 61/448,824, filed on Mar. 3, 2011, provisional application No. 61/418,692, filed on Dec. 1, 2010.

(51) Int. Cl.
| | | |
|---|---|---|
| *A61K 31/7105* | (2006.01) | |
| *C12Q 1/6809* | (2018.01) | |
| *A61K 36/185* | (2006.01) | |
| *A61K 9/00* | (2006.01) | |
| *A61K 35/74* | (2015.01) | |
| *A61K 45/06* | (2006.01) | |

(52) U.S. Cl.
CPC ........ *A61K 31/7105* (2013.01); *A61K 9/0019* (2013.01); *A61K 35/74* (2013.01); *A61K 36/185* (2013.01); *C12Q 1/6809* (2013.01); *A61K 45/06* (2013.01); *A61K 2300/00* (2013.01)

(58) Field of Classification Search
CPC .............. A01K 2207/05; C12N 15/113; C12N 2310/141; A61K 31/7105
See application file for complete search history.

(56) References Cited

U.S. PATENT DOCUMENTS

| | | |
|---|---|---|
| 4,104,373 A | 8/1978 | Sichert |
| 5,925,364 A | 7/1999 | Ribier et al. |
| 6,559,182 B1 | 5/2003 | Purcell |
| 7,063,865 B2 | 6/2006 | Jones et al. |
| 7,964,354 B2 | 6/2011 | Ferguson et al. |
| 8,445,198 B2 | 5/2013 | Knudsen |
| 2006/0240092 A1* | 10/2006 | Breitenkamp ....... A61K 9/1075 424/450 |
| 2007/0122492 A1 | 5/2007 | Behr et al. |
| 2008/0182245 A1 | 7/2008 | Brown |
| 2008/0199420 A1 | 8/2008 | Wendel et al. |
| 2008/0311167 A1 | 12/2008 | Oronsky et al. |
| 2009/0004302 A1 | 1/2009 | Cyr |
| 2009/0253601 A1 | 10/2009 | Tan et al. |
| 2010/0216865 A1* | 8/2010 | Elias .................. C12N 15/1136 514/44 A |
| 2012/0141610 A1 | 6/2012 | Gowey |
| 2012/0201929 A1 | 8/2012 | Guy et al. |
| 2013/0143945 A1* | 6/2013 | Brown .................. C12N 15/111 514/44 A |
| 2015/0157670 A1 | 6/2015 | Kriz et al. |
| 2017/0159108 A1 | 6/2017 | Budding et al. |

FOREIGN PATENT DOCUMENTS

| | | |
|---|---|---|
| EP | 0555691 B1 | 10/1998 |
| WO | WO2014/152932 A1 | 9/2014 |
| WO | WO2017/060794 A1 | 4/2017 |

OTHER PUBLICATIONS

Yang et al. Oncotarget 8: 72835-72846 (Year: 2017).*
Hall et al. Cell Death and Disease 7m e2184, 1-14 (Year: 2016).*
Song et al. Cell Research 23: 274-289 (Year: 2013).*
Jee et al. Brain 135: 1237-1252 (Year: 2012).*
Shao et al., Direct repression of the oncogene CDK4 by the tumor suppressor miR-486-5p in 9 non-small cell lung cancer. Oncotarget. Jun. 7, 2016, vol. 7, No. 23, pp. 34011-3421.
International Search Report Issued for PCT Application No. PCT/US18/57059 dated Feb. 21, 2019.
Sarapin, 2011, https://web.archive.org/web/20101204134909/https://www.drugs.com/drp/sarapin.html.
Mesquita et al., Anti-inflammatory effect of dietary supplementation with omega-3 fatty acids in rats', 2011, Rev. Dor. Sao Paulo, 12: 337-41.
Rahman, Inflammation and the Regulation of Glutathione Level in Lung Epithelial Celis, 1999, Antioxidants & Redox Signaling, 1: 425-447.
Medicalnewstoday, 2017, https://www.medicalnewstoday.com/articles/248423.php.
Martin-Sanchez et al. (2009) Pain Medicine vol. 10, No. 8, 1353-1368.
Comelli et al. (2008) Phytother. Res. 22, 1017-1024.
Harris et al. (2012) BMC Complementary and Alternative Medicine, 12:245.

(Continued)

*Primary Examiner* — Brian Whiteman
(74) *Attorney, Agent, or Firm* — Nguyen Tarbet

(57) ABSTRACT

Compositions and methods for treating a disease are described herein. Compositions having plant preparations, microRNAs, and one or more rate limiters are administered to a patient to promote DNA damage repair and modulate endothelial and mitochondrial function, thereby allowing for healing to occur.

11 Claims, 10 Drawing Sheets
(3 of 10 Drawing Sheet(s) Filed in Color)

Specification includes a Sequence Listing.

(56) References Cited

OTHER PUBLICATIONS

Manchikanti et al. (2004) Pain Physician 7:59-62.
Novak et al. (2001) Flavour Fragr. J. 16: 259-262.
Oomah et al. (2002) Food Chemistry 76: 33-43.
Ross et al. (1996) J. Nat. Prod. 59: 49-51.
Russo et al. (2003) Psychopharmacology 165: 431-432.
John Brittnacher, International Carnivorous Plant Society, http://www.carnivorousplants.org.
Science Finder session began Nov. 7, 2015 at 10:10 am.
Muhammad et al., Antidiabetic Compounds from Sarracenia purpurea Used Traditionally by the Eeyou Istchee Cree First Nation, 2012, J Nat Prod, 75: 1284-1288.
Hensen et al. "Flesh-eating plants". Discover: Science for the curious (Oct. 2001), pp. 1-9. Retrieved fromL <URL: http://discovermagazine.com/2001 /oct/featplants>.
Truth in Aging Web Publication Date: 2006. Retrieved from the Internet: <URL: http://www.truthinaging.com/ingredients/ammonium-acryloyldimethyltaurate>.
Dermis Web Publication Date: 2006. Retrived from the Internet: <URL: http://orgs.dermis.net/content/e05eecdrg/e05news/e686/e706/index_ger.html>.
PCCA Web Publication Date: 2007 <URL: http://www.customcompounding.com.au/wpcontent/uploads/2012/03/VERSABASE-Ingredients.pdf>.
Shrewsbury, R. "Compounding Facilities and Equipment" from Applied Pharmaceutics in Contemporary Compounding: 2nd Edition (2008), pp. 29 and 31-33.
Mody et al. "Isolation of the Insect Paralyzing Agent Coniine from Sarracenia flava". Experientia 32/7 (1976), pp. 829-830.
Preparation of Supposiories. Internet Archive Date: Dec. 11, 2008 [Retrieved from the Internet on: Mar. 24, 2015] .. Retrieved from the Internet: <URL:https://web.archive.org/web/20081211055237 /http://pharmlabs.unc.edu/labs/suppository/bases. html >.
John F Marriott, et.al. Pharmaceutical Compounding and Dispensing. (2006), Chapter 5 (Extemporaneous dispersing), p. 66.
Yuan et al. The expression and function of miRNA-451 in osteosarcoma. Med Oncol (2015) 32:324.

* cited by examiner

Top 30 Human microRNA for each sample:

| | Pre-spine Injection-N 1-Dec UNR18 | | Post-spine injection-N 2-Dec UNR2 | | Pre-spine injection-M 8-Dec UNR13 | | Post-Spine Injection-M 9-Dec UNR30 | | Pre-Spine treatment-M 14-Dec UNR14 | | Post-Spine Injection-M 15-Dec UNR11 | | Pre-Spine injection-Z 23-Dec UNR13 | | Post-Injection spine-Z 22-Dec UNR8 | |
|---|---|---|---|---|---|---|---|---|---|---|---|---|---|---|---|---|
| | microRNA ID | Read | microRNA ID | Read | microRNA ID | Read | microRNA ID | Read | microRNA ID | Read | microRNA ID | Read | microRNA ID | Read | microRNA ID | Read |
| 1 | hsa-mir-10a-5p | 6115 | hsa-mir-10b-5p | 976 | hsa-mir-10b-5p | 7151.5 | hsa-mir-10b-5p | 30493.5 | hsa-mir-10b-5p | 11760.5 | hsa-mir-10b-5p | 4960 | hsa-mir-10b-5p | 5135.5 | hsa-mir-10b-5p | 2891 |
| 2 | hsa-mir-10a-5p | 2554 | hsa-mir-10a-5p | 408 | hsa-mir-10a-5p | 3088.5 | hsa-mir-10a-5p | 7235.5 | hsa-mir-10a-5p | 5381.5 | hsa-mir-10a-5p | 1865 | hsa-mir-10a-5p | 1537.5 | hsa-mir-10a-5p | 1163 |
| 3 | hsa-mir-30a-5p | 2094 | hsa-mir-30a-5p | 321 | hsa-mir-30a-5p | 1654 | hsa-mir-30a-5p | 3856 | hsa-mir-30a-5p | 3406.5 | hsa-mir-30a-5p | 1615 | hsa-mir-30a-5p | 1368.5 | hsa-mir-98a-3p | 652 |
| 4 | hsa-let-7f-5p | 577 | hsa-let-7f-5p | 100 | hsa-let-7f-5p | 616 | hsa-let-7f-5p | 566.5 | hsa-let-7a-5p | 1854.5 | hsa-let-7a-5p | 772.5 | hsa-let-7a-5p | 417.3 | hsa-let-7a-5p | 320 |
| 5 | hsa-let-7a-5p | 496 | hsa-let-7a-5p | 85 | hsa-let-7a-5p | 542 | hsa-mir-182-5p | 482 | hsa-let-7a-5p | 1796 | hsa-let-7a-5p | 666.8333 | hsa-let-7f-5p | 335 | hsa-let-7f-5p | 298 |
| 6 | hsa-mir-30d-3p | 389 | hsa-mir-30d-3p | 75 | hsa-mir-30d-3p | 343 | hsa-mir-100-5p | 399 | hsa-mir-30d-3p | 943 | hsa-let-7f-5p | 373 | hsa-let-7f-5p | 313 | hsa-mir-30d-3p | 170 |
| 7 | hsa-mir-26a-5p | 284 | hsa-mir-26a-5p | 49 | hsa-mir-26a-5p | 336 | hsa-mir-204-5p | 393 | hsa-mir-30d-3p | 485.5 | hsa-mir-30d-3p | 263 | hsa-mir-30d-3p | 195.5 | hsa-mir-26a-5p | 133 |
| 8 | hsa-mir-30a-3p | 287.5 | hsa-mir-30a-3p | 36 | hsa-mir-30a-3p | 185 | hsa-let-7f-5p | 391 | hsa-mir-30a-3p | 435.5 | hsa-mir-30a-3p | 331 | hsa-mir-30a-3p | 194 | hsa-mir-30a-3p | 107 |
| 9 | hsa-let-7b-5p | 235 | hsa-let-7b-5p | 29 | hsa-let-7b-5p | 163 | hsa-mir-30a-3p | 361 | hsa-let-7b-5p | 444 | hsa-let-7b-5p | 220 | hsa-mir-30a-3p | 165 | hsa-let-7b-5p | 83 |
| 10 | hsa-mir-27b-3p | 209 | hsa-mir-27b-3p | 27 | hsa-mir-505-5p | 196 | hsa-let-7b-5p | 327.5 | hsa-mir-335-5p | 388 | hsa-mir-423-3p | 174 | hsa-mir-192-3p | 163.5 | hsa-mir-486-5p | 77 |
| 11 | hsa-mir-375 | 208 | hsa-mir-92a-3p | 21 | hsa-mir-125a-5a | 142 | hsa-mir-26a-5p | 308 | hsa-mir-375 | 383 | hsa-let-7c-5p | 159.8333 | hsa-mir-100-5p | 104 | hsa-let-7c-5p | 73 |
| 12 | hsa-mir-22-3p | 165 | hsa-mir-99b-5p | 20 | hsa-let-7b-3p | 135.5 | hsa-mir-27b-3p | 269 | hsa-mir-30a-5p | 342 | hsa-mir-30a-3p | 145.5 | hsa-mir-423-3p | 83 | hsa-let-7b-5p | 49 |
| 13 | hsa-mir-182-5p | 153.5 | hsa-mir-192-3p | 18 | hsa-mir-27b-3p | 132 | hsa-mir-27b-3p | 254 | hsa-let-7c-5p | 341 | hsa-mir-30a-3p | 145 | hsa-mir-30a-3p | 77 | hsa-let-7c-5p | 47 |
| 14 | hsa-mir-99b-5p | 153 | hsa-mir-182-3p | 16 | hsa-mir-182-3p | 127 | hsa-mir-27b-3p | 253 | hsa-let-7f-5p | 313.5 | hsa-mir-92a-3p | 142.5 | hsa-mir-192-5p | 75 | hsa-mir-92a-3p | 47 |
| 15 | hsa-mir-192-3p | 133 | hsa-mir-375 | 15 | hsa-let-7e-5p | 101 | hsa-let-7e-5p | 184.5 | hsa-mir-100-5p | 311.5 | hsa-mir-100-5p | 123 | hsa-mir-21-5p | 75 | hsa-mir-203a-3p | 46 |
| 16 | hsa-mir-92a-3p | 129 | hsa-mir-27b-5p | 14 | hsa-mir-182-5p | 88.5 | hsa-mir-100-5p | 183 | hsa-mir-100-5p | 280 | hsa-mir-320a | 104.5833 | hsa-mir-203a-3p | 73 | hsa-mir-182-5p | 43 |
| 17 | hsa-let-7g-5p | 124 | hsa-let-7g-5p | 14 | hsa-mir-27b-3p | 86 | hsa-let-7c-5p | 180 | hsa-let-7c-5p | 255.5 | hsa-mir-99b-3p | 100 | hsa-mir-182-5p | 74 | hsa-mir-27b-3p | 45 |
| 18 | hsa-mir-423-3p | 117 | hsa-mir-181-3p | 14 | hsa-mir-181-3p | 85 | hsa-let-7g-5p | 179 | hsa-let-7a-5p | 281 | hsa-mir-146b-3p | 91 | hsa-mir-99a-3p | 70 | hsa-let-7e-5p | 44 |
| 19 | hsa-mir-125a-3p | 113 | hsa-mir-125a-3p | 14 | hsa-mir-192-5p | 84.5 | hsa-let-7g-5p | 171.5 | hsa-mir-27b-3p | 260.5 | hsa-mir-22-3p | 89 | hsa-let-7c-5p | 70 | hsa-mir-192-3p | 39 |
| 20 | hsa-mir-22-3p | 108.5 | hsa-mir-22-3p | 13 | hsa-mir-486-5p | 82 | hsa-mir-486-5p | 171 | hsa-mir-181-5p | 218 | hsa-mir-375 | 88.5 | hsa-mir-182-3p | 65.5 | hsa-mir-182-3p | 38 |
| 21 | hsa-mir-203b-3p | 105 | hsa-let-7c-5p | 12.5 | hsa-mir-30a-3p | 82 | hsa-mir-203a-3p | 164 | hsa-mir-21-5p | 210 | hsa-mir-375 | 85 | hsa-mir-320a | 63.5 | hsa-mir-125a-5p | 34 |
| 22 | hsa-let-7c-5p | 95 | hsa-let-7e-5p | 12 | hsa-let-7c-5p | 80 | hsa-let-7e-5p | 159 | hsa-mir-21-5p | 192.5 | hsa-mir-30a-3p | 74 | hsa-let-7i-5p | 63 | hsa-mir-30a-5p | 32 |
| 23 | hsa-let-7e-5p | 94 | hsa-mir-21-3p | 11 | hsa-mir-21-3p | 77 | hsa-mir-21-3p | 148 | hsa-mir-21-3p | 171 | hsa-mir-30a-3p | 67 | hsa-mir-99a-3p | 55 | hsa-mir-99a-3p | 32 |
| 24 | hsa-mir-100-5p | 93 | hsa-mir-100-5p | 11 | hsa-let-7c-5p | 73 | hsa-mir-100-5p | 145 | hsa-mir-222-3p | 162 | hsa-mir-181a-5p | 64 | hsa-mir-181a-5p | 58 | hsa-mir-181a-5p | 31 |
| 25 | hsa-mir-181a-5p | 81 | hsa-let-7a-5p | 11 | hsa-mir-181a-5p | 71 | hsa-let-7i-5p | 143 | hsa-let-7i-5p | 158 | hsa-mir-182-3p | 63 | hsa-let-7i-5p | 52 | hsa-let-7g-5p | 30 |
| 26 | hsa-let-7i-5p | 76.5 | hsa-let-7c-5p | 10 | hsa-mir-99a-3p | 70 | hsa-mir-99a-3p | 97.5 | hsa-mir-200a-3p | 147 | hsa-mir-23a-3p | 62 | hsa-mir-23a-3p | 51 | hsa-mir-99a-5p | 25 |
| 27 | hsa-let-7g-5p | 70 | hsa-mir-99a-5p | 10 | hsa-mir-181a-3p | 66 | hsa-mir-181a-3p | 85 | hsa-mir-181a-3p | 135 | hsa-mir-23a-3p | 58 | hsa-mir-23a-3p | 50 | hsa-mir-30a-5p | 25 |
| 28 | hsa-mir-21-5p | 68 | hsa-mir-30a-5p | 10 | hsa-mir-22a-3p | 65 | hsa-mir-125a-3p | 81 | hsa-mir-23a-3p | 133 | hsa-mir-23a-3p | 51 | hsa-mir-192-3p | 48 | hsa-mir-204-5p | 23 |
| 29 | hsa-let-7a-5p | 65 | hsa-let-7c-5p | 9 | hsa-mir-200c-3p | 64 | hsa-mir-146b-3p | 70 | hsa-mir-200c-3p | 127 | hsa-mir-98a-3p | 50 | hsa-mir-182-5p | 46 | hsa-let-7g-5p | 23 |
| 30 | hsa-mir-21-5p | 63 | hsa-mir-203a-3p | 7 | hsa-mir-146a-3p | 62 | hsa-mir-181a-3p | 67 | hsa-mir-27a-3p | 132 | hsa-mir-151a-3p | 48 | hsa-mir-151a-5p | 44 | hsa-mir-148a-3p | 22 |

FIG. 3A

| | Pre-Spine-SeI 25-Dec UNR7 | | Post-Spine Injection-SeI 29-Dec UNR1 | |
|---|---|---|---|---|
| | microRNA ID | Read | microRNA ID | Read |
| 1 | hsa-miR-10b-5p | 1992 | hsa-miR-10b-5p | 15224.5 |
| 2 | hsa-miR-30a-5p | 537 | hsa-miR-10a-5p | 6748.5 |
| 3 | hsa-miR-10a-5p | 458 | hsa-miR-30a-5p | 3998 |
| 4 | hsa-miR-21-5p | 117 | hsa-let-7a-5p | 3133.5 |
| 5 | hsa-miR-304-5p | 67 | hsa-let-7f-5p | 2326.5 |
| 6 | hsa-miR-27b-3p | 59.5 | hsa-miR-26a-5p | 1355 |
| 7 | hsa-miR-192-5p | 57.5 | hsa-let-7d-5p | 912 |
| 8 | hsa-let-7f-5p | 52 | hsa-miR-324-5p | 667 |
| 9 | hsa-miR-16a-5p | 47 | hsa-miR-92a-3p | 542 |
| 10 | hsa-miR-203a-3p | 42 | hsa-let-7c-5p | 504.5 |
| 11 | hsa-miR-100-5p | 35 | hsa-miR-30a-3p | 500 |
| 12 | hsa-let-7a-5p | 33 | hsa-miR-192-5p | 485.5 |
| 13 | hsa-let-7b-5p | 32 | hsa-miR-98b-5p | 484 |
| 14 | hsa-miR-148a-3p | 28 | hsa-miR-200b-3s | 395.5 |
| 15 | hsa-miR-30b-3p | 27 | hsa-miR-100-5p | 367.5 |
| 16 | hsa-miR-99b-5p | 26 | hsa-miR-125a-5p | 325 |
| 17 | hsa-miR-200b-3p | 25 | hsa-miR-27b-3p | 322.5 |
| 18 | hsa-let-7g-5p | 22 | hsa-let-7g-5p | 298 |
| 19 | hsa-let-7i-5p | 21 | | 271.3333 |
| 20 | hsa-miR-22-3p | 20 | hsa-miR-191-5p | 215 |
| 21 | hsa-miR-320a | 19 | hsa-miR-181a-5p | 211 |
| 22 | hsa-miR-181a-5p | 16 | hsa-miR-200a-3p | 210 |
| 23 | hsa-miR-575 | 15 | hsa-let-7i-5p | 189 |
| 24 | hsa-miR-146a-5p | 14 | hsa-miR-204-5p | 179 |
| 25 | hsa-miR-200a-3p | 13 | hsa-miR-21-5p | 179 |
| 26 | hsa-miR-151a-3p | 12 | hsa-miR-200c-3p | 178.5 |
| 27 | hsa-miR-182-5p | 11 | hsa-miR-22-3p | 163 |
| 28 | hsa-miR-433-3p | 11 | hsa-miR-182-5p | 156 |
| 29 | hsa-miR-378a-3p | 10 | hsa-miR-148b-5p | 144 |
| 30 | hsa-miR-99a-5p | 10 | hsa-miR-99a-5p | 143.5 |

FIG. 3B

Top 30 Human microRNA for each sample:

| | Curcumin | | Injection Fluid | | Oil | | Plant1 | | Plant2 | |
|---|---|---|---|---|---|---|---|---|---|---|
| | microRNA ID | Read | microRNA ID | Read | microRNA ID | Read | microRNA ID | Read | microRNA ID | Read |
| 1 | hsa-miR-486-5p | 737 | hsa-miR-22-3p | 1980 | hsa-miR-486-5p | 2907 | hsa-miR-10b-5p | 205 | hsa-miR-143-3p | 150 |
| 2 | hsa-miR-191-5p | 86 | hsa-miR-486-5p | 531 | hsa-miR-927-3p | 279 | hsa-miR-10a-5p | 154 | hsa-miR-4454 | 71 |
| 3 | hsa-miR-451a | 40 | hsa-miR-927-3p | 205 | hsa-miR-22-3p | 136 | hsa-miR-143-3p | 46 | hsa-miR-122-5p | 48 |
| 4 | hsa-miR-92a-3p | 23 | hsa-miR-320a | 122.75 | hsa-miR-191-5p | 116 | hsa-miR-100-5p | 34 | hsa-miR-7977 | 35 |
| 5 | hsa-miR-22-3p | 19 | hsa-miR-320b | 108.75 | hsa-miR-451a | 90 | hsa-miR-184 | 29 | hsa-miR-100-5p | 33 |
| 6 | hsa-miR-182-5p | 9 | hsa-let-7b-5p | 86 | hsa-let-7f-5p | 71 | hsa-miR-486-5p | 28 | hsa-miR-486-5p | 32 |
| 7 | hsa-miR-192-5p | 6 | hsa-miR-99b-3p | 59 | hsa-miR-92a-3p | 55 | hsa-miR-99b-5p | 20 | hsa-miR-10a-5p | 27 |
| 8 | hsa-miR-484 | 5 | hsa-let-7f-5p | 46 | hsa-let-7a-5p | 47 | hsa-miR-30a-3p | 14 | hsa-miR-192-5p | 20 |
| 9 | hsa-miR-186-5p | 5 | hsa-miR-92a-3p | 42 | hsa-miR-184 | 38 | hsa-miR-7977 | 10 | hsa-miR-148a-3p | 19 |
| 10 | hsa-miR-25-3p | 3 | hsa-let-7a-5p | 40.5 | hsa-miR-192-3p | 22 | hsa-miR-26a-3p | 9 | hsa-miR-10b-5p | 16 |
| 11 | hsa-miR-300-5p | 3 | hsa-miR-1246 | 30 | hsa-miR-423-5p | 21 | hsa-miR-99b-5p | 6 | hsa-miR-30a-5p | 16 |
| 12 | hsa-miR-100-5p | 3 | hsa-miR-183-5p | 28 | hsa-miR-10a-5p | 16 | hsa-miR-4454 | 5 | hsa-miR-184 | 15 |
| 13 | hsa-miR-185-5p | 3 | hsa-miR-423-5p | 27 | hsa-miR-125b-5p | 16 | hsa-miR-1-3p | 5 | hsa-miR-26a-5p | 9 |
| 14 | hsa-miR-148-3p | 3 | hsa-miR-191-3p | 26 | hsa-miR-25-3p | 16 | hsa-miR-125a-5p | 5 | hsa-let-7f-5p | 8 |
| 15 | hsa-let-7a-5p | 2 | hsa-miR-26a-3p | 24 | hsa-miR-182-5p | 15 | hsa-let-7i-5p | 5 | hsa-miR-99a-5p | 7 |
| 16 | hsa-miR-423-5p | 2 | hsa-miR-182-3p | 23 | hsa-miR-20a-5p | 15 | hsa-miR-182-5p | 5 | hsa-miR-101-3p | 7 |
| 17 | hsa-miR-26a-5p | 2 | hsa-miR-125b-5p | 21 | hsa-miR-320a | 13 | hsa-miR-192-5p | 4 | hsa-miR-191-5p | 6 |
| 18 | hsa-miR-381a-5p | 2 | hsa-miR-100-5p | 20 | hsa-let-7b-5p | 13 | hsa-miR-191-5p | 4 | hsa-miR-204-5p | 6 |
| 19 | hsa-miR-363-3p | 2 | hsa-miR-103a-3p | 20 | hsa-miR-30e-5p | 11 | hsa-miR-927-3p | 4 | hsa-miR-1-3p | 5 |
| 20 | hsa-miR-423-3p | 2 | hsa-let-7g-5p | 17 | hsa-miR-21-5p | 9 | hsa-miR-379 | 4 | hsa-miR-1246 | 5 |
| 21 | hsa-miR-99b-5p | 2 | hsa-miR-27b-3p | 15 | hsa-miR-192-5p | 9 | hsa-let-7f-5p | 3.5 | hsa-miR-99b-5p | 4 |
| 22 | hsa-miR-23a-3p | 2 | hsa-miR-143-3p | 15 | hsa-miR-30e-5p | 9 | hsa-miR-204-5p | 3 | hsa-miR-22-3p | 4 |
| 23 | hsa-miR-425-5p | 2 | hsa-miR-146a-5p | 14 | hsa-miR-101-3p | 9 | hsa-miR-27b-3p | 3 | hsa-miR-145-5p | 4 |
| 24 | hsa-miR-937-3p | 1 | hsa-miR-184 | 12 | hsa-miR-484 | 8 | hsa-let-7g-5p | 3 | hsa-miR-27b-3p | 4 |
| 25 | hsa-let-7f-5p | 1 | hsa-miR-203a-3p | 12 | hsa-let-7g-5p | 7 | hsa-miR-125b-5p | 3 | hsa-miR-4286 | 4 |
| 26 | hsa-let-7i-5p | 1 | hsa-miR-148a-3p | 12 | hsa-miR-100-5p | 6 | hsa-miR-24-3p | 3 | hsa-let-7a-5p | 3 |
| 27 | hsa-miR-128-3p | 1 | hsa-miR-192-3p | 11 | hsa-miR-185-5p | 6 | hsa-miR-132-3p | 3 | hsa-let-7g-5p | 3 |
| 28 | hsa-miR-142-5p | 1 | hsa-miR-151a-3p | 10 | hsa-miR-7-5p | 5 | hsa-miR-183-5p | 3 | hsa-miR-125b-5p | 3 |
| 29 | hsa-miR-30b-5p | 1 | hsa-miR-28-3p | 10 | hsa-miR-146a-5p | 5 | hsa-miR-148a-3p | 2 | hsa-miR-937-3p | 2 |
| 30 | hsa-miR-145-5p | 1 | hsa-let-7i-5p | 9 | hsa-miR-27b-3p | 4 | hsa-miR-101-3p | 2 | hsa-miR-125a-5p | 2 |

FIG. 4A

Top 30 Human microRNA for each sample (cont.)

FIG. 4B

Top 30 Human microRNA for each sample:

| | Pre miR 22/937/486 CT | | Post miR 22/937/486 CT | |
|---|---|---|---|---|
| | G24 | | G25 | |
| | microRNA ID | Read | microRNA ID | Read |
| 1 | hsa-miR-10b-5p | 28859 | hsa-miR-10b-5p | 10383 |
| 2 | hsa-miR-10a-5p | 12619.5 | hsa-miR-10a-5p | 3247 |
| 3 | hsa-miR-100-5p | 4144.5 | hsa-miR-30a-5p | 632 |
| 4 | hsa-let-7f-5p | 3808 | hsa-let-7f-5p | 397 |
| 5 | hsa-let-7a-5p | 3046 | hsa-miR-100-5p | 346 |
| 6 | hsa-miR-30a-5p | 2607 | hsa-let-7a-5p | 274 |
| 7 | hsa-miR-99b-5p | 2501 | hsa-miR-99b-5p | 272 |
| 8 | hsa-miR-192-5p | 2042.5 | hsa-miR-203a-3p | 210 |
| 9 | hsa-miR-99a-5p | 1621 | hsa-miR-99a-5p | 192 |
| 10 | hsa-miR-26a-5p | 1320 | hsa-miR-26a-5p | 171 |
| 11 | hsa-miR-203a-3p | 1237 | hsa-let-7g-5p | 153 |
| 12 | hsa-miR-27b-3p | 1024.5 | hsa-miR-192-5p | 142 |
| 13 | hsa-miR-375 | 940 | hsa-let-7b-5p | 141 |
| 14 | hsa-let-7b-5p | 776 | hsa-miR-30d-5p | 135 |
| 15 | hsa-let-7g-5p | 711 | hsa-miR-191-5p | 119 |
| 16 | hsa-miR-30a-3p | 708 | hsa-miR-21-5p | 116 |
| 17 | hsa-miR-191-5p | 582 | hsa-miR-148a-3p | 100 |
| 18 | hsa-miR-200b-3p | 579 | hsa-miR-27b-3p | 85 |
| 19 | hsa-miR-30d-5p | 500 | hsa-miR-200c-3p | 77 |
| 20 | | 444 | hsa-miR-30b-5p | 72 |
| 21 | hsa-miR-200c-3p | 428 | hsa-miR-200b-3p | 67 |
| 22 | hsa-miR-148a-3p | 427 | hsa-miR-486-5p | 58 |
| 23 | hsa-miR-146b-5p | 401 | hsa-miR-320a | 53.83333 |
| 24 | hsa-let-7c-5p | 367 | hsa-miR-30a-3p | 53 |
| 25 | hsa-let-7i-5p | 365 | hsa-miR-30c-5p | 53 |
| 26 | hsa-miR-21-5p | 314 | hsa-miR-4485-3p | 51 |
| 27 | hsa-miR-378a-3p | 310.5 | hsa-miR-375 | 43 |
| 28 | hsa-miR-22-3p | 304 | hsa-let-7c-5p | 42 |
| 29 | hsa-miR-92a-3p | 278 | hsa-miR-378a-3p | 42 |
| 30 | hsa-miR-24-3p | 271 | hsa-miR-182-5p | 42 |

| | Oil extract |
|---|---|
| | G POE |
| hsa-let-7a-2-3p | N/A |
| hsa-let-7a-3p | N/A |
| hsa-let-7a-5p | 33.61 |
| hsa-let-7b-3p | 39.04 |
| hsa-let-7b-5p | 34.02 |
| hsa-let-7c-3p | N/A |
| hsa-let-7c-5p | 35.24 |
| hsa-let-7d-3p | N/A |
| hsa-let-7d-5p | N/A |
| hsa-let-7e-3p | N/A |
| hsa-let-7e-5p | N/A |
| hsa-let-7f-1-3p | N/A |
| hsa-let-7f-2-3p | N/A |
| hsa-let-7f-5p | 34.05 |
| hsa-let-7g-3p | N/A |
| hsa-let-7g-5p | N/A |
| hsa-let-7i-3p | N/A |
| hsa-let-7i-5p | N/A |
| hsa-miR-10a-3p | N/A |
| hsa-miR-10a-5p | 36.38 |
| hsa-miR-10b-3p | 35.19 |
| hsa-miR-10b-5p | N/A |
| hsa-miR-26a-5p | 34.21 |
| hsa-miR-27b-3p | N/A |
| hsa-miR-30a-3p | N/A |
| hsa-miR-30a-5p | N/A |
| hsa-miR-30b-3p | N/A |
| hsa-miR-30b-5p | 36.88 |
| hsa-miR-30c-1-3p | N/A |
| hsa-miR-30c-2-3p | N/A |
| hsa-miR-30c-5p | 35.80 |
| hsa-miR-30d-3p | N/A |
| hsa-miR-30d-5p | 37.35 |
| hsa-miR-30e-3p | N/A |
| hsa-miR-30e-5p | N/A |
| hsa-miR-92a-3p | 36.10 |
| hsa-miR-99a-3p | N/A |
| hsa-miR-99a-5p | N/A |
| hsa-miR-99b-3p | N/A |
| hsa-miR-99b-5p | 35.12 |
| hsa-miR-100-5p | G POE |
| hsa-miR-101-3p | N/A |
| hsa-miR-101-5p | N/A |
| hsa-miR-125a-5p | 39.16 |
| hsa-miR-148a-3p | N/A |
| hsa-miR-182-5p | N/A |
| hsa-miR-191-5p | 40.06 |
| hsa-miR-192-5p | 33.57 |
| hsa-miR-200c-5p | N/A |
| hsa-miR-200c-3p | 35.34 |
| hsa-miR-375 | 40.32 |
| hsa-miR-378a-3p | N/A |
| hsa-miR-486-5p | 33.73 |
| hsa-miR-4485 | 33.43 |
| | 19.34 |
| IPC | 19.39 |
| | 19.12 |

FIG. 5

| Pre miR 22/937/486 CT | | Post miR 22/937/486 CT | | Plant | |
|---|---|---|---|---|---|
| G24 | | G25 | | | |
| microRNA ID | Read | microRNA ID | Read | microRNA ID | Read |
| hsa-miR-22-3p | 304 | hsa-miR-22-3p | 37 | hsa-miR-22-3p | 485 |
| hsa-miR-486-5p | 205 | hsa-miR-486-5p | 58 | hsa-miR-486-5p | 68 |
| hsa-miR-937-3p | 0 | hsa-miR-937-3p | 5 | hsa-miR-937-3p | 0 |

FIG. 6A

| | hsa-miR-22-3p | hsa-miR-486-5p | hsa-miR-937-3p |
|---|---|---|---|
| 1 uL | 33.63 | 2.58 | 10.5 |
| 2 uL | 33.5 | 2.31 | 9.71 |
| 5 uL | 34.57 | 2.09 | 8.89 |
| PosC | 19.32 | 2.34 | 28.54 |

FIG. 6B

SEQUENCE LISTING

```
<160> NUMBER OF SEQ ID NOS: 37

<210> SEQ ID NO 1
<211> LENGTH: 22
<212> TYPE: RNA
<213> ORGANISM: Homo sapiens

<400> SEQUENCE: 1
ugagguagua gguuguauag uu                                          22

<210> SEQ ID NO 2
<211> LENGTH: 22
<212> TYPE: RNA
<213> ORGANISM: Homo sapiens

<400> SEQUENCE: 2
ugagguagua gguugugugg uu                                          22

<210> SEQ ID NO 3
<211> LENGTH: 22
<212> TYPE: RNA
<213> ORGANISM: Homo sapiens

<400> SEQUENCE: 3
ugagguagua gguuguaugg uu                                          22

<210> SEQ ID NO 4
<211> LENGTH: 22
<212> TYPE: RNA
<213> ORGANISM: Homo sapiens

<400> SEQUENCE: 4
ugagguagga gguuguauag uu                                          22

<210> SEQ ID NO 5
<211> LENGTH: 22
<212> TYPE: RNA
<213> ORGANISM: Homo sapiens

<400> SEQUENCE: 5
ugagguagua gauuguauag uu                                          22

<210> SEQ ID NO 6
<211> LENGTH: 22
<212> TYPE: RNA
<213> ORGANISM: Homo sapiens

<400> SEQUENCE: 6
ugagguagua guuuguacag uu                                          22

<210> SEQ ID NO 7
<211> LENGTH: 22
<212> TYPE: RNA
```

-continued

<213> ORGANISM: Homo sapiens

<400> SEQUENCE: 7
ugagguagua guuugugcug uu                                           22

<210> SEQ ID NO 8
<211> LENGTH: 23
<212> TYPE: RNA
<213> ORGANISM: Homo sapiens

<400> SEQUENCE: 8
uacccuguag auccgaauuu gug                                          23

<210> SEQ ID NO 9
<211> LENGTH: 23
<212> TYPE: RNA
<213> ORGANISM: Homo sapiens

<400> SEQUENCE: 9
uacccuguag aaccgaauuu gug                                          23

<210> SEQ ID NO 10
<211> LENGTH: 22
<212> TYPE: RNA
<213> ORGANISM: Homo sapiens

<400> SEQUENCE: 10
aagcugccag uugaagaacu gu                                           22

<210> SEQ ID NO 11
<211> LENGTH: 22
<212> TYPE: RNA
<213> ORGANISM: Homo sapiens

<400> SEQUENCE: 11
aacccguaga uccgaacuug ug                                           22

<210> SEQ ID NO 12
<211> LENGTH: 21
<212> TYPE: RNA
<213> ORGANISM: Homo sapiens

<400> SEQUENCE: 12
uacaguacug ugauaacuga a                                            21

<210> SEQ ID NO 13
<211> LENGTH: 24
<212> TYPE: RNA
<213> ORGANISM: Homo sapiens

<400> SEQUENCE: 13
ucccugagac ccuuuaaccu guga                                         24

<210> SEQ ID NO 14
<211> LENGTH: 22
<212> TYPE: RNA
<213> ORGANISM: Homo sapiens

<400> SEQUENCE: 14
ucagugcacu acagaacuuu gu                                           22

<210> SEQ ID NO 15
<211> LENGTH: 24

```
<212> TYPE: RNA
<213> ORGANISM: Homo sapiens

<400> SEQUENCE: 15
uuuggcaaug guagaacuca cacu                                          24

<210> SEQ ID NO 16
<211> LENGTH: 23
<212> TYPE: RNA
<213> ORGANISM: Homo sapiens

<400> SEQUENCE: 16
caacggaauc ccaaaagcag cug                                           23

<210> SEQ ID NO 17
<211> LENGTH: 21
<212> TYPE: RNA
<213> ORGANISM: Homo sapiens

<400> SEQUENCE: 17
cugaccuaug aauugacagc c                                             21

<210> SEQ ID NO 18
<211> LENGTH: 22
<212> TYPE: RNA
<213> ORGANISM: Homo sapiens

<400> SEQUENCE: 18
uaauacugcc ugguaaugau ga                                            22

<210> SEQ ID NO 19
<211> LENGTH: 23
<212> TYPE: RNA
<213> ORGANISM: Homo sapiens

<400> SEQUENCE: 19
uaauacugcc ggguaaugau gga                                           23

<210> SEQ ID NO 20
<211> LENGTH: 22
<212> TYPE: RNA
<213> ORGANISM: Homo sapiens

<400> SEQUENCE: 20
uucaaguaau ccaggauagg cu                                            22

<210> SEQ ID NO 21
<211> LENGTH: 21
<212> TYPE: RNA
<213> ORGANISM: Homo sapiens

<400> SEQUENCE: 21
uucacagugg cuaaguucug c                                             21

<210> SEQ ID NO 22
<211> LENGTH: 22
<212> TYPE: RNA
<213> ORGANISM: Homo sapiens

<400> SEQUENCE: 22
cuuucagucg gauguuugca gc                                            22

<210> SEQ ID NO 23
```

```
<211> LENGTH: 22
<212> TYPE: RNA
<213> ORGANISM: Homo sapiens

<400> SEQUENCE: 23
uguaaacauc cucgacugga ag                                              22

<210> SEQ ID NO 24
<211> LENGTH: 22
<212> TYPE: RNA
<213> ORGANISM: Homo sapiens

<400> SEQUENCE: 24
cugggagaag gcuguuuacu cu                                              22

<210> SEQ ID NO 25
<211> LENGTH: 23
<212> TYPE: RNA
<213> ORGANISM: Homo sapiens

<400> SEQUENCE: 25
uguaaacauc cuacacucuc agc                                             23

<210> SEQ ID NO 26
<211> LENGTH: 22
<212> TYPE: RNA
<213> ORGANISM: Homo sapiens

<400> SEQUENCE: 26
uguaaacauc cccgacugga ag                                              22

<210> SEQ ID NO 27
<211> LENGTH: 22
<212> TYPE: RNA
<213> ORGANISM: Homo sapiens

<400> SEQUENCE: 27
uguaaacauc cuugacugga ag                                              22

<210> SEQ ID NO 28
<211> LENGTH: 22
<212> TYPE: RNA
<213> ORGANISM: Homo sapiens

<400> SEQUENCE: 28
uuuguucguu cggcucgcgu ga                                              22

<210> SEQ ID NO 29
<211> LENGTH: 22
<212> TYPE: RNA
<213> ORGANISM: Homo sapiens

<400> SEQUENCE: 29
acuggacuug gagucagaag gc                                              22

<210> SEQ ID NO 30
<211> LENGTH: 20
<212> TYPE: RNA
<213> ORGANISM: Homo sapiens

<400> SEQUENCE: 30
uaacggccgc gguacccuaa                                                 20
```

```
<210> SEQ ID NO 31
<211> LENGTH: 22
<212> TYPE: RNA
<213> ORGANISM: Homo sapiens

<400> SEQUENCE: 31
uccuguacug agcugccccg ag                                              22

<210> SEQ ID NO 32
<211> LENGTH: 22
<212> TYPE: RNA
<213> ORGANISM: Homo sapiens

<400> SEQUENCE: 32
uauugcacuu gucccggccu gu                                              22

<210> SEQ ID NO 33
<211> LENGTH: 22
<212> TYPE: RNA
<213> ORGANISM: Homo sapiens

<400> SEQUENCE: 33
aacccguaga uccgaucuug ug                                              22

<210> SEQ ID NO 34
<211> LENGTH: 22
<212> TYPE: RNA
<213> ORGANISM: Homo sapiens

<400> SEQUENCE: 34
cacccguaga accgaccuug cg                                              22

<210> SEQ ID NO 35
<211> LENGTH: 22
<212> TYPE: RNA
<213> ORGANISM: Homo sapiens

<400> SEQUENCE: 35
auccgcgcuc ugacucucug cc                                              22

<210> SEQ ID NO 36
<211> LENGTH: 23
<212> TYPE: RNA
<213> ORGANISM: Homo sapiens

<400> SEQUENCE: 36
aaggagcuua caaucuagcu ggg                                             23

<210> SEQ ID NO 37
<211> LENGTH: 22
<212> TYPE: RNA
<213> ORGANISM: Homo sapiens

<400> SEQUENCE: 37
caacuagacu gugagcuucu ag                                              22
```

MICRO-RNA PROFILING, COMPOSITIONS, AND METHODS OF TREATING DISEASES

CROSS REFERENCE

This application is a continuation-in-part and claims benefit of U.S. patent application Ser. No. 15/791,147 filed Oct. 23, 2017, which claims priority to U.S. Patent Application No. 62/411,439, filed Oct. 21, 2016, the specification(s) of which is/are incorporated herein in their entirety by reference.

U.S. patent application Ser. No. 15/791,147 is also a continuation-in-part and claims benefit of U.S. patent application Ser. No. 15/420,374, filed on Jan. 31, 2017, which is a continuation-in-part and claims benefit of U.S. patent application Ser. No. 14/990,107, filed on Jan. 7, 2016, which is a continuation-in-part and claims benefit of U.S. patent application Ser. No. 14/306,581, filed on Jun. 17, 2014, which is a non-provisional of U.S. Provisional Patent Application No. 61/835,749, filed Jun. 17, 2013, the specification(s) of which is/are incorporated herein in their entirety by reference.

U.S. patent application Ser. No. 14/990,107 is also a continuation-in-part and claims benefit of U.S. patent application Ser. No. 14/305,933, filed on Jun. 16, 2014, which is a non-provisional of U.S. Provisional Patent Application No. 61/835,741, filed Jun. 17, 2013, the specification(s) of which is/are incorporated herein in their entirety by reference.

U.S. patent application Ser. No. 14/990,107 is also a continuation-in-part and claims benefit of U.S. patent application Ser. No. 13/309,144, filed on Dec. 1, 2011, which is a non-provisional of U.S. Provisional Patent Application No. 61/448,824, filed Mar. 3, 2011, and U.S. Provisional Patent Application No. 61/418,692, filed Dec. 1, 2010, the specification(s) of which is/are incorporated herein in their entirety by reference.

REFERENCE TO SEQUENCE LISTING

Applicant asserts that the paper copy of the Sequence Listing is identical to the Sequence Listing in computer readable form found on the accompanying computer file, entitled GOWB_16_03_CIP_Sequence_ST25. The content of the sequence listing is incorporated herein by reference in its entirety.

FIELD OF THE INVENTION

The present invention relates to microRNA profiling, in particular, plant microRNA mapping to human microRNA and compositions and methods of treating diseases and maintaining homeostasis.

BACKGROUND OF THE INVENTION

MicroRNA (miRNA) are small non-coding RNA molecules that contain nucleotides. miRNA are found in plants, animals and some viruses, and have varying purposes known throughout the literature. For example, miRNA can function in RNA silencing and post-transcriptional regulation of gene expression. Their role in regulation of gene and protein expression has led researchers to study miRNA for their potential in identification and resolution of disease states. There are nearly 2000 identified miRNA in the human genome, and as such, they have very complex interactions to maintain proper gene and protein function. These systems of miRNA are not static but dynamic, and change with need for tissue repair or healing. For example, miRNA can bind to and regulate fibroblast growth factors (FGF).

In nature, plants can maintain themselves without human intervention. They strive to maintain the balance of miRNA necessary for growth, development, and reproduction, while only shifting their miRNA profiles if needed. Conventional medicine describes diseases as a manifestation of biological dysfunctions in the body. Disease states tend to be caused by low DNA repair and imbalances of miRNA profiles, with miRNA being too high or too low relative to normal controls. For example, miRNAs that tend to be high in cancer include miRNA-7, miRNA-10, and miRNA-30, whereas a miRNA that tends to be low in cancerous conditions is miRNA-486, which is needed to regulate DNA repair. Further still, a person's DNA requires particular nutrients in order to repair damage, maintain health, and to be free of disease in the body.

The present invention feature methods and compositions for treating diseases, inflammation, repairing DNA damage, and regulating endothelial and mitochondrial function by decreasing the miRNA profile (such as when a glutathione formulation is used) to drop levels overall. During the drop, healing can occur, which may be due to a shift in the genome caused by administering the compositions of the invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

In some aspects, the present invention features compositions and methods for repairing DNA damage. In one embodiment, the composition may comprise microRNA (miR)-486 and glutathione, said composition referred to herein as Sarravis. In other embodiments, Sarravis may further include magnesium, selenium, zinc, cysteine, or manganese. Without wishing to limit the invention to a particular theory or mechanism, the present invention has found that an overall rise in the miRNA genome indicates disease, and healthier subjects have lower levels in their miRNA profiles. Thus, the compositions of the invention may be administered to a patient in need of treating a disease.

While there are many nutrients, such as vitamins, minerals, and co-factors, necessary for health, the present invention has discovered key nutrients, referred to herein as "rate limiters", that are consistently lacking in patients. If a rate limiter level is too low, then the miRNA genome will rise overall. Each patient tends to struggle with keeping sufficient levels of one or more rate limiters in order to maintain homeostasis, or freedom from disease states. When these nutrients are restored in the patient, the clinical results have shown resolution of symptoms and disease of the patient. These rate limiters that must be present in the patient consist of glutathione, cysteine, magnesium, zinc, selenium, and magnesium.

In some aspects, the rate limiters can be applied topically as creams, lotions or oils, or using intravenous, subcutaneous, or intramuscular medicines. In other aspects, the patient may consume foods or drink water having said rate limiters. For instance, the extracellular matrix (ECM) must have ions to maintain cytoskeletal connection to DNA. Since the body is primarily water, then drinking water with the rate limiters can treat or even prevent disease states.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 3A shows the pre and post microRNA profiles of patients that received spine injections of each of niacin (N), magnesium (M), and zinc (Z).

FIG. 3B shows the pre and post microRNA profiles of a patient that received spine injections of selenium (Sel).

FIG. 4A shows the microRNA profiles of curcumin, Sarapin® (Injection Fluid), sweet almond oil infused with *S. flava* tincture (Oil), 4-day old *S. flava* (Plant1), and 4-day old *S. purpurea* (Plant2).

FIG. 4B shows the microRNA profiles of an *S. flava* tincture (Tincture1), an *S. purpurea* tincture (Tincture2), an *S. leukophylla* tincture (Tincture3), a *Sarracenia* hybrid tincture (Tincture4), and a pre microRNA profile of a relatively healthy person. Note in the plant tinctures that levels of miR-184, miR-937, miR-486 and miR-22 are high. FIG. 4B also shows the post-microRNA profiles of the same two patients in TABLE 4 after administering the *Sarracenia flava* tincture (UrineA, UrineB); note that the miR-486 levels has significantly increased in both patients. Furthermore, each patient's disease was resolved.

FIG. 5 shows the pre and post microRNA profiles (G24, G25) of a patient that received spine injections of miR-22, miR-937, and miR-486. FIG. 5 also shows the microRNA profile of a $CO_2$ extracted dried *S. flava* that was 4-days old (Oil Extract).

FIG. 6A shows a summary of how miR-22, miR-937, and miR-486 shifts in the patient with the spine injections.

FIG. 6B shows the corresponding Cq value of RT-qPCR of miR-22, miR-937, and miR-486. For Cq value, the lower the value indicates higher starting count. All three microRNAs were detected in the sterile solutions provided. Note the small numbers, indicating higher starting count in the sterile solutions. The sterile solutions only had 1.5 nm per 30 ml vial.

DESCRIPTION OF PREFERRED EMBODIMENTS

Figure 1:
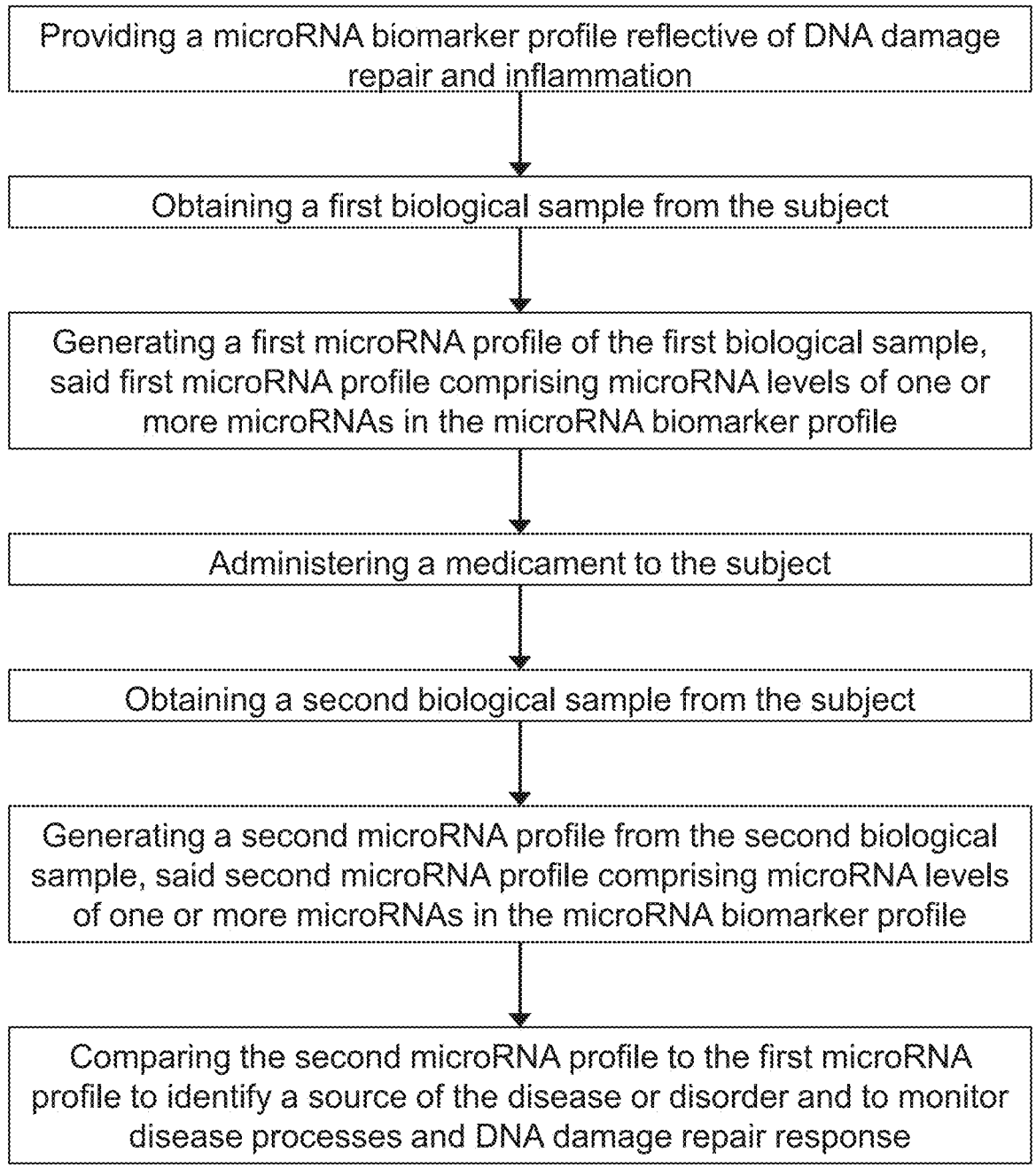
FIG. 1 shows an algorithm of an embodiment of the present invention.
Figure 2:
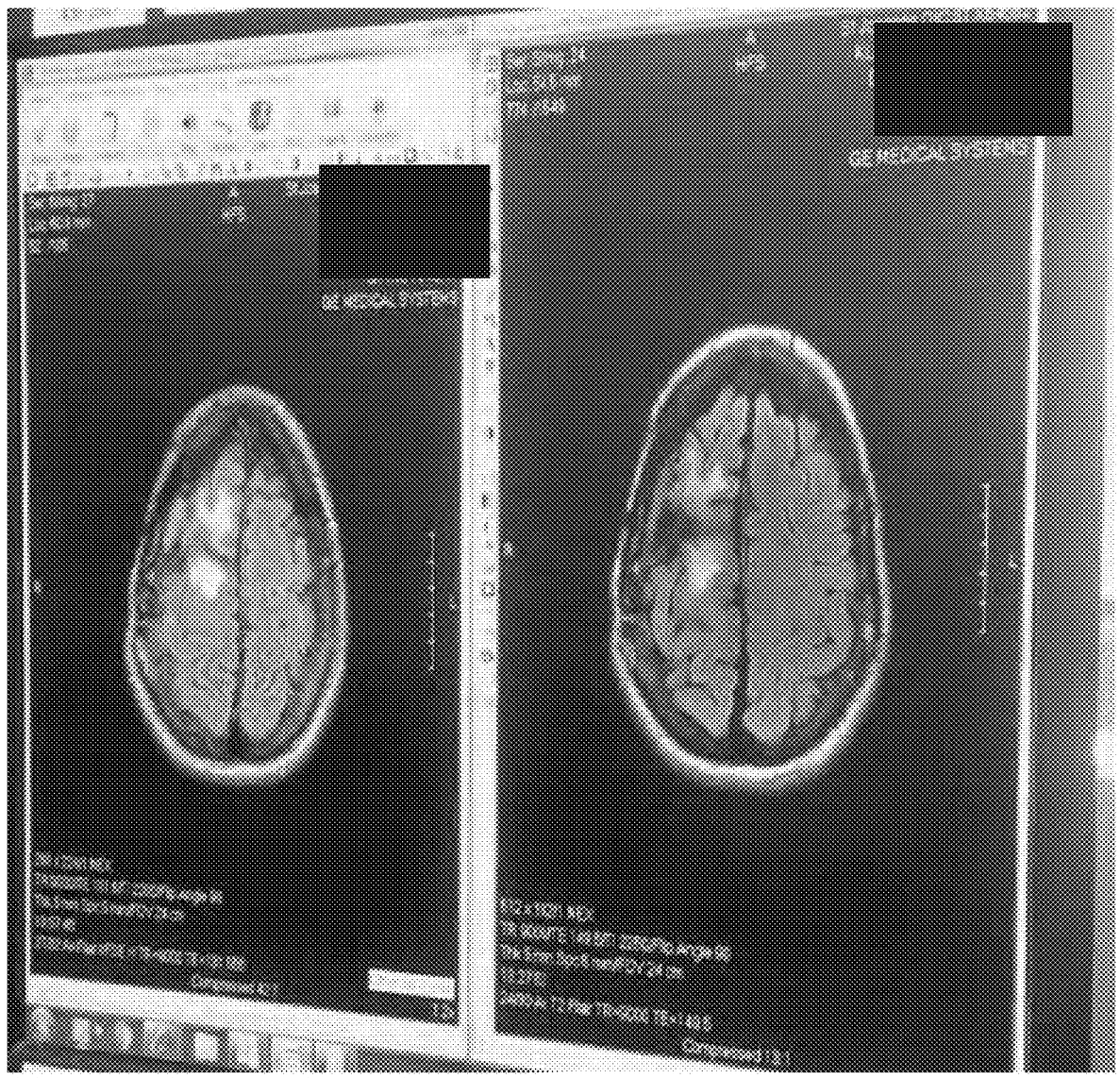
FIG. 2 shows MRI images for a brain tumor. The image on the left was in March 2016 prior to treatment. A composition of miRNA-86 and glutathione (referred to as Sarravis CT Spine) was injected in to the spine and a follow up MRI was taken in July 2016, right image, which clearly shows a shift in the tumor.
Figures 7A, 7B:
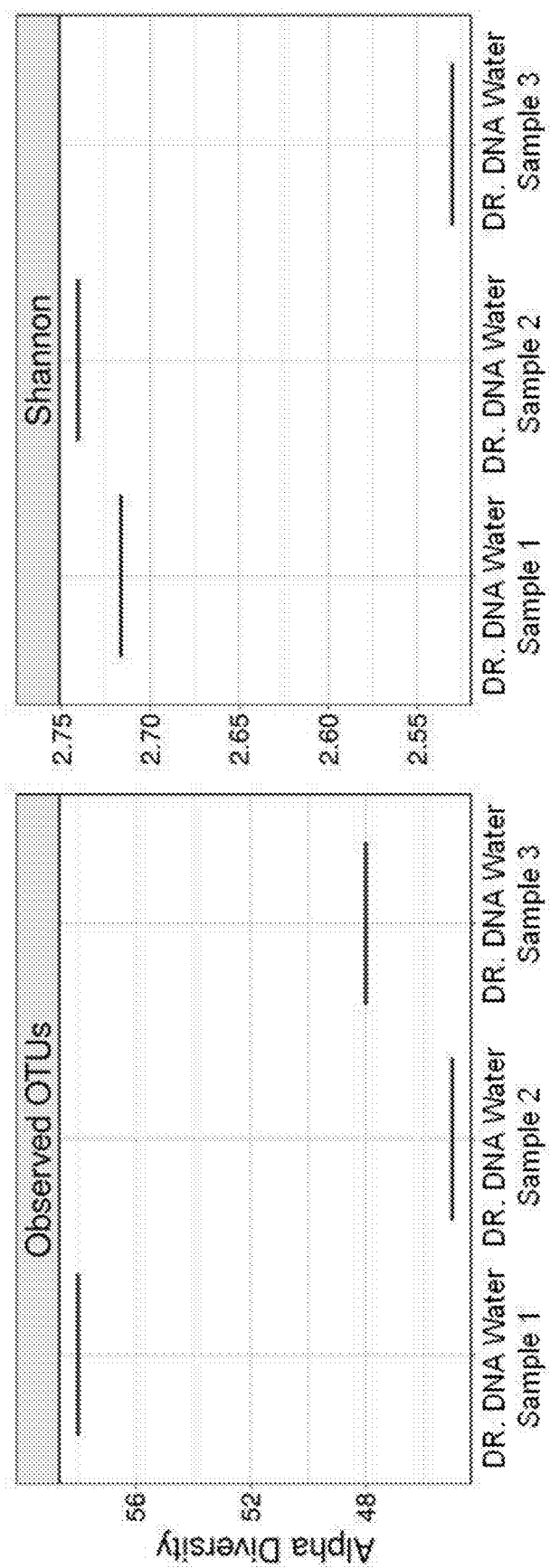
FIGS. 7A and 7B are results of an alpha diversity of three DR. DNA water samples using Observed Operational Taxonomic Units (OTUs) and Shannon diversity index, respectively. Alpha diversity is a measurement of bacterial richness and evenness in a sample, i.e. within-sample diversity. OTU is a measurement of microbial richness within a sample, i.e. number of different species in a community. Shannon Diversity Index accounts for the evenness (how close in numbers are each species in an environment) and the richness; the higher the index, the higher the diversity.

The International Carnivorous Plant Society (www.carnivorousplants.org) defines a "carnivorous plant" as a predatory plant that obtains its nutrients by trapping and killing prey. A carnivorous plant has the following features: 1. the plant captures and kills its prey; 2. the plant has some mechanism to digest the prey; and 3. the plant absorbs the nutrients from the prey.

As used herein, the term "extract" is defined as a separation of the beneficial (medicinal) components of an herb from the fibrous, less useful part of the plant. Extracts can be in a liquid, gel, or powdered form.

As used herein, the term "infuse" is defined as a procedure of withdrawing nutritive compounds of an herb into a medium, and allowing them to linger in the medium for a period of time to allow for the transfer of herbal extracts into the medium. An "infused solution" is the resulting solution with the nutritive compounds.

As used herein, the term "tincture" is defined as a heavily concentrated extract made by placing chopped fresh or dried herbs into a container and covering them with a solvent. The mixture is then sealed and allowed to macerate for several weeks.

As used herein, a "plant preparation" may be an extract, tincture, or infused solution made or prepared from a plant. The plant preparation contains the active components from the plant. For example, the plant preparation of a pitcher plant may be a pitcher plant extract, tincture, or infused solution. An active component is extracted from the plant. As used herein, an "active component" is defined as the beneficial (medicinal) plant parts/material.

As used herein, the term "supplement" are generally understood include, but are not limited to, vitamins, minerals, fiber, fatty acids, amino acids and amine derivatives. As used herein, the term "minerals" may be categorized into two kinds of minerals: macrominerals and trace minerals. Macrominerals include, but are not limited to, calcium, phosphorus, magnesium, sodium, potassium, chloride and sulfur. Trace minerals include, but are not limited to, iron, manganese, copper, iodine, zinc, cobalt, fluoride and selenium. Examples of vitamins include, but are not limited to, retinoic acid (Vitamin A), vitamin B-complex, vitamin C, vitamin D, vitamin E, and vitamin K. Non-limiting examples of fatty acids include phosphocholine, phosphytidylcholine, and phosphytidylserine. Non-limiting examples of amino acids include cysteine and arginine, such as L-arginine. Examples of amine derivatives include, but are not limited to, glucosamine.

As used herein, the terms "administering" or "administer" is defined as the introduction of a substance (composition) into cells in vitro or into the body of an individual in vivo and includes topical, oral, nasal, ocular, rectal, vaginal and parenteral routes. The composition of the present invention may be administered via any route of administration, including but not limited to topical, subcutaneous, intramuscular, intravenous, intradermal, intranasal, orally, or by consumption of food or water.

As defined herein, the terms "treating" or "treatment" of a condition includes: (1) preventing the condition, i.e., causing the clinical symptoms of the condition not to develop in a mammal that may be exposed to or predisposed to the condition but does not yet experience or display symptoms of the condition; (2) inhibiting the condition, i.e., arresting or reducing the development of the condition or its clinical symptoms; or (3) ameliorating or relieving the condition, i.e., causing regression of the condition or its clinical symptoms. As used herein, the terms "treat" or "treatment" refer to both therapeutic treatment or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented or onset delayed. Optionally, the patient may be identified (e.g., diagnosed) as one suffering from the disease or condition prior to administration of the composition of the invention.

As used herein, the term "homeostasis" refers to the ability to regulate variables such that conditions remain stable and relatively constant.

As used herein, Cytenssic® means "cell essence", and Cytenssic® therapy is a treatment developed in the present invention. The principle of Cytenssic® therapy is that the body is able to heal itself.

As used herein, the term "Sarravis" refers to a composition comprising miR-486-5p (miR-486) and glutathione, which is a base composition of the present invention. In some embodiments, the Sarravis composition may comprise at least 0.001 nmol/ml of miR-486 and at least 0.001 mg/ml of glutathione. In other embodiments, the Sarravis composition may comprise at least 0.05 nmol/ml of miR-486 and at least 0.01 mg/ml of glutathione.

In one embodiment, the Sarravis composition may comprise an herbal preparation of *Sarracenia flava*. In another embodiment, the Sarravis composition may comprise an herbal preparation of *Sarracenia purpurea*. The term "Sarravis" may collectively refer to both compositions. However, when Sarravis is used for spine injections, the composition is referred to herein as "Sarravis CT Spine" specifically for the composition comprising an herbal preparation of *Sarracenia purpurea*. While each composition may be derive from a different *Sarracenia* species, both compositions may comprise the base composition of miR-486-5p (miR-486) and glutathione.

As used herein, the term "therapeutically effective amount" refers to an amount of a compound, i.e. the composition, effective to treat a condition, disease or disorder in a subject, or reduce (i.e., slow to some extent and preferably stop) and/or relieve, to some extent, one or more of the symptoms associated with a disorder or disease. The "therapeutically effective amount" will vary depending on the compound, the condition and its severity and body factors such as age, weight, etc., of the subject to be treated.

As used herein, a "solution" is defined as is a homogeneous mixture composed of two or more substances. A "solute" is a substance dissolved in another substance, known as a "solvent".

A "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects.

As used herein, "those defined above" and "those defined herein" when referring to a variable incorporates by reference the broad definition of the variable as well as any narrow and/or preferred, more preferred and most preferred definitions, if any.

As used herein, the term "hsa-let-7" refers to the miRNA of the hsa-let-7 family or series as shown in TABLE 1. As used herein, the term "miR-10" refers to the miRNA of the miR-10 family or series as shown in TABLE 1. As used herein, the term "miR-30" refers to the miRNA of the miR-30 family or series as shown in TABLE 1. As used herein, the term "miR-99" refers to the miRNA of the miR-99 family or series as shown in TABLE 1.

TABLE 1 lists miRNA sequences obtained from mirnadb.org.

| SEQ ID NO. | mRNA | mRNA Sequence |
|---|---|---|
| 1 | hsa-let-7a-5p | UGAGGUAGUAGGUUGUAUAGUU |
| 2 | hsa-let-7b-5p | UGAGGUAGUAGGUUGUGUGGUU |
| 3 | hsa-let-7c-5p | UGAGGUAGUAGGUUGUAUGGUU |
| 4 | hsa-let-7e-5p | UGAGGUAGGAGGUUGUAUAGUU |
| 5 | hsa-let-7f-5p | UGAGGUAGUAGAUUGUAUAGUU |
| 6 | hsa-let-7g-5p | UGAGGUAGUAGUUUGUACAGUU |
| 7 | hsa-let-7i-5p | UGAGGUAGUAGUUUGUGCUGUU |
| 8 | hsa-miR-10a-5p | UACCCUGUAGAUCCGAAUUUGUG |
| 9 | hsa-miR-10b-5p | UACCCUGUAGAACCGAAUUUGUG |
| 10 | hsa-miR-22-3p | AAGCUGCCAGUUGAAGAACUGU |
| 11 | hsa-miR-100-5p | AACCCGUAGAUCCGAACUUGUG |
| 12 | hsa-miR-101 | UACAGUACUGUGAUAACUGAA |
| 13 | hsa-miR-125a-5p | UCCCUGAGACCCUUUAACCUGUGA |
| 14 | hsa-miR-148a-3p | UCAGUGCACUACAGAACUUUGU |
| 15 | hsa-miR-182-5p | UUUGGCAAUGGUAGAACUCACACU |
| 16 | hsa-miR-191-5p | CAACGGAAUCCCAAAAGCAGCUG |
| 17 | hsa-miR-192-5p | CUGACCUAUGAAUUGACAGCC |
| 18 | hsa-miR-200b-3p | UAAUACUGCCUGGUAAUGAUGA |
| 19 | hsa-miR-200c-3p | UAAUACUGCCGGGUAAUGAUGGA |
| 20 | hsa-miR-26a-5p | UUCAAGUAAUCCAGGAUAGGCU |
| 21 | hsa-miR-27b-3p | UUCACAGUGGCUAAGUUCUGC |
| 22 | hsa-miR-30a-3p | CUUUCAGUCGGAUGUUUGCAGC |
| 23 | hsa-miR-30a-5p | UGUAAACAUCCUCGACUGGAAG |
| 24 | hsa-miR-30c-2-3p | CUGGGAGAAGGCUGUUUACUCU |
| 25 | hsa-miR-30c-5p | UGUAAACAUCCUACACUCUCAGC |

TABLE 1-continued lists miRNA sequences obtained from mirnadb.org.

| SEQ ID NO. | mRNA | mRNA Sequence |
|---|---|---|
| 26 | hsa-miR-30d-5p | UGUAAACAUCCCCGACUGGAAG |
| 27 | hsa-miR-30e-5p | UGUAAACAUCCUUGACUGGAAG |
| 28 | hsa-miR-375 | UUUGUUCGUUCGGCUCGCGUGA |
| 29 | hsa-miR-378a-3p | ACUGGACUUGGAGUCAGAAGGC |
| 30 | hsa-miR-4485-3p | UAACGGCCGCGGUACCCUAA |
| 31 | hsa-miR-486-5p | UCCUGUACUGAGCUGCCCCGAG |
| 32 | hsa-miR-92a-3p | UAUUGCACUUGUCCCGGCCUGU |
| 33 | hsa-miR-99a-5p | AACCCGUAGAUCCGAUCUUGUG |
| 34 | hsa-miR-99b-5p | CACCCGUAGAACCGACCUUGCG |
| 35 | hsa-miR-937-3p | AUCCGCGCUCUGACUCUCUGCC |
| 36 | hsa-miR-708-5p | AAGGAGCUUACAAUCUAGCUGGG |
| 37 | hsa-miR-708-3p | CAACUAGACUGUGAGCUUCUAG |

MicroRNA Profiling

MicroRNAs regulate DNA and protein function in their ability to silence genes (according to most research and definitions). However, they are particles that come directly from encoded regions within the DNA and as such, should be seen more as DNA communication signals. They have the ability to communicate, from one DNA to another and from one protein to (or from) the DNA, what needs to happen for the genetic code to manifest properly. miRNA levels are known to change in disease states and can be profiled from the patient to identify excess or deficiencies. As shown in TABLE 2, miRNA can regulate gene expression for many biological functions.

TABLE 2

| Biological Function | Regulating miRNA |
|---|---|
| Endothelial function | 100, 10, 186, 1, 200 family, 224, 140, 146, 335, 7, 122, 30, 99, 27, 151, 126, 101, 127, 184, 22, 24 |
| Mitochondrial function | 100, 143, 185, 21, 181, 499, 7, 30 |
| Matrix metalloproteinases (MMPs) | 774, 100, 143, 205, 25, 140, 148, 30 |
| p53 | miRNA 486 for DNA repair at GI/S |
| Stem cell | 100, 143, 937, 124, 205, 205, 140, 146, 499, 486, 7, 99, 151, 126, 378, 125, 127, 184, 22, 29, 133 |
| Endothelial to mesenchyme transition | 100 (actually increases it), 143 (actually decreases it which puts 100 in balance/check), 10, 185, 182, 186, 200 family, 181, 191,7, 122, 30, 151, 101, 184, 22, 133 |
| Sugar homeostasis | 100, 143, 1, 26, 185, 375, 486, 151, 378 |
| Fats | 1143, 183, 182, 375, 486, 27, 378 |
| Fats/cholesterol | 182, 375, 486, 27, 378, 26, 185, 189 |
| Cell division/repair/ cytochrome p450 | 744, 1, 192, 122, 325 |
| Nervous system | 744, 10, 1, 185, 182, 375, 7, 184 |
| Eye function | 182, 203, 184 |
| Muscle | 1, 25, 140, 499, 30? 378 |
| Lung | 185, 499 |
| Skin | 25, 126 |
| Gastroenterological | 151, 375, 122, 30, 378 |

TABLE 2-continued

| Biological Function | Regulating miRNA |
|---|---|
| Bone | 140, 30, 126, 22 |
| Cardiovascular | 26, 151, 185, 25, 21, 499, 122, 27, 184 |
| Orthopedic structure | 124, 140, 499, 375, 30, 101, 184 |
| Apoptosis | 100, 143, 221, 25, 375, 423, 21, 146, 499, 7, 122, 126, 101, 378, 125, 184, 22, 24 |
| Cytokine | 100, 26, 185, 182, 375, 21, 140, 146, 181, 375, 192 |
| Wnt signaling | 27, 29, 483, 744, 22, 184, 124, 100, 185, 182, 200 family, 375, 22, 184 |
| Hormone | 26, 124, 205, 375, 191, 122, 378, 92, 127, 22 |
| Mitosis | 100, 423, 486, 148, 30, 151, 101 |
| DNA Repair | 143, 26, 182, 221, 1908, 21, 146, 486, 151, 99, 7 |

Rate Limiters

The healing and building process requires key nutrients in order to occur. These are nutrients found within the extracellular matrix (ECM) and glycolytic pathways (glycolysis, citric acid cycle, ETS). While there are many nutrients contained within said system, the specific nutrients that tend to be the most needed within mammalian systems include, but are not limited to, magnesium for DNA repair, glutathione as a cofactor for mitochondrial function, zinc for p53 protein folding, selenium for DNA repair, and cysteine for cytochrome P450 and for building of FGFs. These nutrients are referred to herein as "Rate Limiters". Magnesium is required in the ECM as it is needed by cells for DNA stabilization therefore the FGF/FB system will look for this within the ECM in order to heal and build tissues. A common side effect of too-low magnesium is scar tissue and inflammation. Deficiencies in rate limiters can bring symptoms or disease patterns since the body has strayed away from homeostasis. Patients may be lacking all these or some of these, or parts of some of these rate limiters. Diet is important for providing Rate Limiters. If the diet is high in processed sugars, healing is hampered due to changes in cytokines, which then harms the DNA (e.g. DNA damage).

According to some embodiments, the present invention features a composition for repairing DNA damage. In some embodiments, the composition may comprise one or more miRNAs, which are selected by comparing the miRNA profiles of plants with that of human miRNA to determine which miRNA are lacking or missing from the human miRNA, and one or more rate limiters.

In one embodiment, the composition may comprise at least about 0.001 nmol/ml of microRNA(miR)-486, and one or more rate limiters selected from a group consisting of magnesium, selenium, zinc, glutathione, cysteine, and manganese. In other embodiments, the one or more rate limiters may be present in an amount of at least 0.001% wt/vol in the composition. The composition may be in a suitable form for administration, such as an injectable solution, an intravenous solution, an oral formulation such as an oral solution or pill, a sublingual formulation such as a lozenge, or a topical cream, lotion, or oil.

In some embodiments, the miR-486 may be derived from turmeric, *Sarracenia flava*, *Sarracenia purpurea*, or hybrids thereof, or a non-human animal source. In other embodiments, the miR-486 is a synthetic miR-486. In further embodiments, the composition may also comprise miR-22, miR-100, miR-937, or a combination thereof. In one embodiment, the miRNAs may be derived from plant or non-human animal sources. In another embodiment, the miRNAs may be synthetically prepared. Some non-limiting examples of plants include *Sarracenia* spp., turmeric, lilies, and orchids. Examples of non-human animals from which the miRNA profiles can be obtained from include, but are not limited to, cows, birds, fish, reptiles, insects, and amphibians.

In another embodiment, the composition may comprise at least about 0.001 nmol/ml of microRNA(miR)-486, and at least about 0.001% wt/vol glutathione, herein referred to as Sarravis. In further embodiments, the composition may also comprise one or more rate limiters selected from a group consisting of magnesium, selenium, zinc, cysteine, and manganese, in an amount of at least 0.001% wt/vol in the composition.

According to yet another embodiment, the composition for repairing DNA damage may comprise at least about 0.001 mg/ml magnesium, at least about 0.001 mg/ml selenium, at least about 0.001 mg/ml zinc, and at least about 0.001 mg/ml glutathione. In other embodiments, the composition may also comprise at least about 0.001 mg/ml cysteine or at least about 0.001 mg/ml manganese. In further embodiments, the composition may also comprise at least about 0.001 nmol/ml of one or more microRNAs (miR) selected from a group consisting of miR-22, miR-100, miR-937, and miR-486.

In some embodiments, the ranges of rate limiters in the composition can vary depending on the route of administration. For instance, a sublingual formulation may have trace amounts of the rate limiters, such as 0.001 mg to 0.1 per lozenge, whereas a topical formulation may have several grams/ml.

According to other embodiments, the present invention features a method for treating inflammation in a subject in need of such treatment. The method may comprise administering to the subject a therapeutically-effective amount of any of the compositions described herein. In some embodiments, the composition may be administered intravenously, intramuscularly, subcutaneously, orally, sublingually, or topically.

In some embodiments, the present invention may further feature a food product comprising a supplemental component. The supplemental component may comprise any of the compositions described herein. Examples of food products having the supplemental component include, but are not limited to, nutritional bars, candies, processed, dietary staple and grains, rice, and baked goods.

DR. DNA Drinking Water

As previously mentioned, when people are sick, there is an overall elevation in microRNA which reflects inflammation in the endothelium. When studying the profile to see how overactive the endothelium is, miR-10, miR-7, and miR-30 are typically high for those who are sick relative to symptom free subjects. Current technologies are studying drugs to stabilize the endothelium. Without wishing to limit the invention to a particular theory, it is believed that conventional drugs cannot stabilize the endothelium because of the need of the DNA of the endothelial cells for minerals, and their connection to the ECM is too intricate via the integrin/mineral network.

According to some embodiments, the present invention may feature a drinking water product (DR. DNA water) comprising potable water to which has been added a composition comprising magnesium, selenium, zinc, and glutathione. In further embodiments, cysteine and/or manganese may also be added to the DR. DNA water. The DR. DNA water with rate limiters can stabilize the overactive endothelium because of its water structure, minerals, and pH, thus causing healing responses.

In other embodiments of the present invention, the composition for repairing DNA damage may comprise at least about 0.001 mg/ml magnesium, at least about $10^{-5}$ mg/ml selenium, at least about $10^{-5}$ mg/ml zinc, and at least about 0.001 mg/ml glutathione. Said composition may be added to potable water to produce the DR. DNA water product. In still other embodiments, the composition may further comprise at least about 0.001 nmol/ml of one or more microRNAs (miR) selected from a group consisting of miR-22, miR-100, miR-937, and miR-486. The one or more miRs may be added to the DR. DNA water. In yet other embodiments, the composition may further comprise at least about $10^{-5}$ mg/ml cysteine or at least about $10^{-5}$ mg/ml manganese, which may also be added to the DR. DNA water.

Again, without wishing to limit the invention to a particular theory, the Rate Limiters can change the water molecule structure and "program" the water to be endothelial protecting and DNA damage response enhancing (DDR), which are two factors that are required for water to be healing. For example, magnesium is vital for regulating endothelial functions, and as soon as magnesium levels drop, inflammation is signaled via endothelial DNA cells. Selenium and zinc may also be added to water in order to enhance its DDR properties. Endothelial levels may increase with the glutathione, which is an important antioxidant, and cysteine may modulate cytochrome P450. Manganese is required for integrin function, which is the protein network that solidifies the connection between the DNA and the extracellular matrix.

In one embodiment, a non-limiting example of a composition that may be use in intravenous administration may comprise the following: 200-300 cc of normal saline, 800-1000 mg of magnesium, 2-5 mg of zinc, 0.5-1 mg of selenium, 50-100 mg of n-acetyl cysteine (NAC), and 2-5 mg of manganese. The minerals of said composition may be in its salt form, such as chloride or sulfate. In a further embodiment, miRNA, glutathione or both may be added to the composition. The above intravenous composition is but one example, and other compositions may have different amounts of rate limiters and miRNA. In preferred embodiments, the range of said rate limiters and miRNA can be tailored to a patient's specific needs.

In another embodiment, a non-limiting example of a composition that may be use for injection into or near joints in the extremities to treat injuries may comprise the following: equal parts, such a 1-5 cc, of each rate limiter having a concentration of 500-1000 mg/ml for magnesium, 2-5 mg/ml for zinc, 0.5-1 mg/ml for selenium, 50-100 mg/l for NAC, 2-5 mg/ml for manganese, 200-500 mg/ml for glutathione. The minerals of said composition may be in its salt form, such as chloride or sulfate. In a further embodiment, miRNA, such as miR-486, miR-22, miR-937, or miR-100, may be added to the composition. The injectable composition is but one example, and other compositions may have different amounts of rate limiters and miRNA. In preferred embodiments, the range of said rate limiters and miRNA can be tailored to a patient's specific needs.

In yet another embodiment, a non-limiting example of a composition that may be use for injection at or near the spine may comprise 75% of Sarravis CT Spine, and the remainder having equals parts of miR-22, miR-937, and miR-100. In another embodiment, the spine injection may comprise a composition having 50% of miR-486, 25% miR-100, and 25% of 100 mg/ml NAC. Without wishing to be bound by theory, the spine injections are believed to treat systemic diseases. For instance, the spine injection may resolve plantar fasciitis or stop tumor growth. Further still, the spine injections may be impacting the mitochondria In some embodiments, the treatments may be combined such that two different compositions are administered to the patient. For instance, the spine injections may be administered with the IV treatment, or with the joint injection as previously described.

In some embodiments, the composition may comprise a single rate limiter, such as glutathione. This glutathione composition may be injected near the spine. In other embodiments, the composition may comprise a single miRNA or a whole plant miRNA profile. For example, the composition may comprise miR-486 to be administered near the spine for use in DNA damage repair. As another example, the composition may comprise the whole plant miRNA profile, such as that of a *Sarracenia* plant.

In preferred embodiments, the composition may comprise a combination of miRNA and rate limiters to achieve optimal results for spine injection treatments. Without wishing to be bound to a particular theory, the miRNA can be regulated by the rate limiters, thus the combination of the two can have improve efficacy than when they are administered separately. For example, the composition may comprise miRNA, such as miR-22, miR-486, and/or miR-937, with glutathione, cysteine and/or manganese.

In further embodiments, any of the compositions of the present invention may further comprise vitamins such as, for example, vitamin B, vitamin C, niacinamide, or any other water-soluble vitamin, in amounts ranging from 0.001-100 mg/ml.

According to another embodiment, the composition may further comprise one or more plant preparations. For example, the plant preparation is obtained from a carnivorous plant such as *Sarracenia flava, Sarracenia purpurea, Sarracenia leukophyll*, or hybrids thereof. In other embodiments, the plant preparation may be obtained from curcumin, lilies, orchids, or combinations thereof. As another example, the plant preparation may comprise *Rose damascena*, which may provide p53 support or cytochrome p450 support. In further embodiments, any suitable plant may be used in making the plant preparations. In still other embodiments, the composition may further comprise cannabinoids, vitamins, minerals, micronutrients, antioxidants, proteins (i.e. amino acids), protein derivatives, or combinations thereof.

According to some embodiments, the present invention features a method for diagnosing a disease or disorder or tracking progression thereof in a subject. The method may comprise providing a microRNA biomarker profile reflective of DNA damage repair and inflammation, obtaining a first biological sample from the subject, generating a first microRNA profile of the first biological sample comprising microRNA levels of one or more microRNAs in the microRNA biomarker profile, administering a medicament to the subject, obtaining a second biological sample from the subject, generating a second microRNA profile from the second biological sample comprising microRNA levels of one or more microRNAs in the microRNA biomarker profile, and comparing microRNA trends and levels between the first microRNA profile and the second microRNA profile to identify a source of the disease or disorder and to monitor disease processes and DNA damage repair response. In preferred embodiments, the microRNA biomarker profile may comprise hsa-let-7, miR-10, hsa-miR-22-3p, miR-100-5p, miR-101, miR-125a-5p, miR-148a-3p, miR-182-5p, miR-191-5p, miR-192-5p, miR-200-c, miR-26a-5p, miR-27b-3p, miR-30, miR-375, miR-378a-3p, miR-4485-3p, miR-486-5p, miR-937-3p, miR-92a-3p, and miR-99.

In one embodiment, the test sample may be a blood, saliva, or urine sample. In another embodiment, the medicament may comprise Sarravis. In yet another embodiment, the medicament may comprise magnesium, selenium, zinc, cysteine, glutathione, manganese, or a combination thereof. In a further embodiment, the medicament may comprise one or more microRNAs (miR) selected from a group consisting of miR-22, miR-100, miR-937, and miR-486. In other embodiments, the medicament may further comprise vitamins, minerals, and amino acids.

In some embodiments, the medicament may be effective for modulating microRNA levels when administered to the subject. In other embodiments, the microRNA trends and levels are indicative of nutrient levels in the subject. Further still, the microRNAs of the microRNA biomarker profile are further reflective of endothelial and mitochondrial functionality.

In preferred embodiments, the composition may be administered by subcutaneous or intramuscular injection near or above a spine of the subject. Without wishing to limit the invention to a particular mechanism, administering the composition near or above the spine was found to be a more effective mechanism of stimulating genome shift.

According to other embodiments, the present invention features a method for formulating a patient-specific medicament for treating a disease or disorder in said patient needing such treatment. The method may comprise providing a microRNA biomarker profile reflective of DNA damage repair and inflammation, obtaining a first biological sample from the patient, generating a first microRNA profile comprising microRNA levels of one or more microRNAs in the microRNA biomarker profile, administering, to the patient, a preliminary composition comprising Sarravis or miR-486 or glutathione alone, obtaining a second biological sample from the patient comprising microRNA levels of one or more microRNAs in the microRNA biomarker profile, comparing the second microRNA profile to the first microRNA profile to identify one or more target microRNAs indicative of which rate limiters or microRNA is deficient in the patient, and preparing the patient-specific medicament by adding the rate limiters or microRNA that is deficient in the patient to the preliminary composition. In preferred embodiments, a therapeutically-effective amount of the medicament may be administered to the patient to promote healing and DNA damage repair, thereby treating the disease or disorder in the patient.

In some embodiments, the microRNA biomarker profile may comprise hsa-let-7, miR-10, hsa-miR-22-3p, miR-100-5p, miR-101, miR-125a-5p, miR-148a-3p, miR-182-5p, miR-191-5p, miR-192-5p, miR-200-c, miR-26a-5p, miR-27b-3p, miR-30, miR-375, miR-378a-3p, miR-4485-3p, miR-486-5p, miR-937-3p, miR-92a-3p, and miR-99. In other embodiments, the microRNAs that are effective for DNA damage repair is selected from a group consisting of miR-22, miR-100, miR-486, and miR-937.

In one embodiment, the first biological sample or the second biological sample may be a blood, saliva, or urine sample. In another embodiment, the patient-specific medicament may be prepared by adding magnesium, selenium, zinc, cysteine, manganese, or a combination thereof to the preliminary composition. In a further embodiment, the preliminary composition or the patient-specific medicament may be administered by subcutaneous or intramuscular injection near or above a spine.

In some embodiments, the microRNA added to the preliminary composition may be effective for modulating DNA damage repair, endothelial, and mitochondrial function. When levels of the target microRNAs in the first microRNA profile are substantially greater than that of the corresponding microRNAs in the second microRNA profile, this is indicative of deficient levels of rate limiters. Examples of said target microRNAs include hsa-let-7 family, miR-10 family, or miR-30 family.

In some embodiments, the invention provides a method of preparing an injectable medicine for treating a disease or disorder in a subject. The method may comprise selecting one or more plant or bacterial microRNA extracts, and combining therapeutic amounts of said one or more plant or bacterial microRNA extracts in sterile water to produce the injectable medicine. Without wishing to limit the present invention, the medicine may be effective for promoting healing and DNA damage repair when injected into the subject, thereby treating the disease or disorder. In preferred embodiments, the medicine may be administered by subcutaneous or intramuscular injection near or above a spine of the subject.

In one embodiment, the step of selecting the one or more plant or bacterial microRNA extracts may comprise providing a microRNA biomarker profile reflective of DNA damage repair and inflammation, obtaining a first biological sample from the patient, generating a first microRNA profile comprising microRNA levels of one or more microRNAs in the microRNA biomarker profile, administering to the patient a preliminary composition comprising miR-486, glutathione, or a combination of miR-486 and glutathione, obtaining a second biological sample from the patient comprising microRNA levels of one or more microRNAs in the microRNA biomarker profile, comparing the second microRNA profile to the first microRNA profile to identify one or more target microRNAs indicative of which rate limiters or microRNAs are deficient in the patient, and providing one or more plant or bacterial microRNA extracts based on the microRNAs that are deficient in the patient. In some embodiments, the microRNA biomarker profile may comprise hsa-let-7, miR-10, hsa-miR-22-3p, miR-100-5p, miR-101, miR-125a-5p, miR-148a-3p, miR-182-5p, miR-191-5p, miR-192-5p, miR-200-c, miR-26a-5p, miR-27b-3p, miR-30, miR-375, miR-378a-3p, miR-4485-3p, miR-486-5p, miR-937-3p, miR-92a-3p, and miR-99.

In some embodiments, the plant or bacterial microRNA extracts comprises miR-22, miR-100, miR-937, miR-486, or a combination thereof. In other embodiments, the method may further comprise adding vitamins, minerals, amino acids, or a combination thereof to the injectable medicine. In yet other embodiments, the method may further comprise adding magnesium, selenium, zinc, cysteine, glutathione, manganese, miR-708, or a combination thereof to the injectable medicine.

In some embodiments, the miRNAs may be derived from plant or non-human animal sources. In other embodiments, the miRNA may be synthetic mimics. In some embodiments, the compositions or medicines described herein may comprise plant-sourced miRNAs, bacterial-sourced miRNAs, or non-human animal sourced miRNAs, synthetic miRNA mimics, or combinations thereof. As a non-limiting example, the injectable medicine may comprise miR-486 extracted from pitcher plants and a synthetic miR-708 mimic.

According to further embodiments, the present invention features a method of microRNA profiling a plant to human microRNAs. The method may comprise obtaining a plant sample from a plant, and mapping microRNAs in said plant sample to human microRNAs to identify target microRNAs of the plant sample that appear in the human microRNAs, thus generating a plant microRNA profile comprising the target microRNAs. In some embodiments, the step of mapping the microRNAs may comprise assaying plant sample and matching the plant miRNAs to human miRNAs to identify the human miRNA content in said plant sample. In some embodiments, the plant microRNA profile may include levels of the target microRNAs, such as hsa-let-7, miR-10, hsa-miR-22-3p, miR-100-5p, miR-101, miR-125a-5p, miR-148a-3p, miR-182-5p, miR-191-5p, miR-192-5p, miR-200-c, miR-26a-5p, miR-27b-3p, miR-30, miR-375, miR-378a-3p, miR-4485-3p, miR-486-5p, miR-937-3p, miR-92a-3p, and miR-99. Without wishing to limit the invention to a particular theory, the target microRNAs are effective for modulating DNA damage repair, endothelial, and mitochondrial function. In further embodiments, the method may include the step of isolating and extracting one or more of the target microRNAs from the plant sample. The plant sample may be an extract of the plant, such as a tincture. Preferably, the plant sample can be obtained from any suitable plant. Examples of plants include, but are not limited to, *Sarracenia* spp., Orchidaceae plants, *Lilium* plants, or *Rosa* plants. After extraction, the one or more of the target microRNAs can be prepared into a medicament that promotes DNA damage repair.

Without wishing to be bound by a particular theory or mechanism, the elevations of patient miRNA profiles prior to instigation of any treatment may be based on shifts in rate limiter loads. For example if miR-30 is high, this may indicate low cysteine and/or selenium. If miR-7 is high, this may indicate low zinc. If miR-10 is high, this may indicate low magnesium. In preferred embodiments, when looking at the overall profile, the types of miRNA that are too high, and whether or not miR-486 is low, is reflective of a patient's disease state.

Without wishing to limit the invention to a particular theory or mechanism, it was discovered that miR-486 (miR-486-5p) is effecting for DNA damage repair. For instance, when pitcher plant or curcumin tinctures were administered to patients, a rise in miR-486 was observed and the patient's symptoms decreased, labs improve, etc.

In some embodiment, miRNA pre-treatment and post-treatment profiles with the use of spine injections having different miRNA and rate limiters, miR-486 had increased with the use of zinc. Zinc had lowered all other miRNA level with the injection, except miR-486.

TABLE 3 summarizes the overall effect of rate limiters on the genome.

| RATE LIMITER | Impact on genome using spine injections |
| --- | --- |
| Magnesium | Increases all miRNA |
| Zinc | Decrease all miRNA except miR-486 |
| Selenium | Increases all miRNA |
| Cysteine | Increases all miRNA |
| Glutathione | Decrease all miRNA |

In preferred embodiments, the method is effective for treating the disease such as, but certainly not limited to, an autoimmune disease, Hashimoto disease, diabetes, anemia, tumors, inflammation and cancer.

Without wishing to limit the invention to any theory or mechanism, it is believed that the technical feature of the present invention advantageously provides for medicines that can introduce miRNA that a patient is lacking or missing, and thereby re-establish balance, which can lead to resolution of disease. None of the presently known prior references or work has the unique inventive technical feature of the invention.

Another embodiment of the present invention features a method of regulating microRNA (miRNA) homeostasis for treating a disease in a subject in need of such treatment. The method may comprise measuring miRNA levels in the subject, assaying non-human miRNA profiles and mapping said profiles to human miRNA to identify their human miRNA content, preparing a composition comprising the non-human miRNA that the subject is lacking or having low levels thereof, in an acceptable carrier, and administering the composition to the subject to re-establish miRNA homeostasis, thereby resolving the disease. The non-human miRNA profiles can be obtained from plants or non-human animals. In some embodiments, the composition may further comprise one or more plant preparations. For instance, the plant preparation may be obtained from a carnivorous plant such as *Sarracenia flava, Sarracenia purpurea, Sarracenia leukophyl*, or hybrids thereof. Further examples of plant preparations include, but are not limited to, curcumin, lilies, rose, orchids, or combinations thereof. In other embodiments, the composition may further comprise cannabinoids, vitamins, minerals, micronutrients, antioxidants, proteins (i.e. amino acids), protein derivatives, or combinations thereof.

According to another embodiment, the present invention features a composition for regulating homeostasis in a subject. The composition may comprise one or more miRNA profiles, wherein the miRNA profiles are selected by comparing the miRNA profiles with that of human miRNA to determine which miRNA are lacking or missing from the human miRNA, and one or more rate limiters. The composition can be effective for adjusting homeostatic levels in the subject. In one embodiment, the rate limiters may be magnesium, glutathione, zinc, selenium, and cysteine. In one embodiment, the one or more miRNA profiles may be derived from plant miRNA. Some non-limiting examples of said plant miRNA profiles may be obtained from *Sarracenia* spp., curcumin, lilies, and orchids. In another embodiment, the one or more miRNA profiles may be derived from non-human animal miRNA. Examples of non-human animals from which the miRNA profiles can be obtained from include, but are not limited to, cows, birds, fish, reptiles, insects, and amphibians.

In preferred embodiments, medicines should be complex profiles of miRNA, not just a single or small grouping of a few miRNA. Without wishing to limit the invention to a particular theory or mechanism, miRNA homeostasis (i.e. balance) in a subject can be achieved by use of miRNA medicines obtained by full plant profiles of miRNA. Current plant research focuses on the identification of miRNA specific to that plant. However, if plants are studied to identify the human miRNA content, then a homogolous medicine may be made to introduce the miRNA that are missing into humans or animals and re-establish balance, therefore the resolution of disease.

Human miRNA profiles tend to demonstrate low levels of miRNA, such as 100, and 486, even though they are vital to DNA repair. One can observe this in the miRNA profiles of "Urine A" and "Urine B" of TABLE 4. Note the lack and/or low amounts of miRNA needed for DNA repair and p53 function.

TABLE 4

Pre microRNA profiles of two patients prior to administering a *Sarracenia flava* tincture (UrineA - gout, UrineB - autoimmune thyroiditis), note that the miR-486 levels were less than 50 for both patients.

| UrineA | | UrineB | |
|---|---|---|---|
| microRNA ID | Read | microRNA ID | Read |
| hsa-miR-10b-5p | 18440.5 | hsa-miR-10b-5p | 3431.5 |
| hsa-miR-10a-5p | 8150.5 | hsa-miR-10a-5p | 1790.5 |
| hsa-miR-30a-5p | 2849.5 | hsa-let-7b-5p | 964 |
| hsa-miR-99b-5p | 2099 | hsa-let-7a-5p | 874.5 |
| hsa-let-7a-5p | 1939.5 | hsa-miR-203a-3p | 723 |
| hsa-let-7b-5p | 1719.5 | hsa-miR-27b-3p | 697 |
| hsa-miR-26a-5p | 1538 | hsa-miR-99a-5p | 627 |
| hsa-miR100-5p | 1474.5 | hsa-miR-30a-5p | 529.5 |
| hsa-miR-192-5p | 1097 | hsa-miR-26a-5p | 480 |
| hsa-miR-30d-Sp | 922.5 | hsa-miR-200b-3p | 406 |
| hsa-let-7f-5p | 856 | hsa-let-7f-5p | 390 |
| hsa-miR-99a-5p | 833.5 | hsa-let-7c-5p | 348 |
| hsa-miR-375 | 782 | hsa-miR-100-5p | 293 |
| hsa-miR-125a-5p | 780 | hsa-miR-99b-5p | 261 |
| hsa-miR-191-5p | 691 | hsa-iniR-148a-3p | 256 |
| hsa-let-7c-5p | 636.5 | hsa-miR-320a | 232.25 |
| hsa-miR-125b-5p | 471 | hsa-miR-423-5p | 207 |
| hsa-miR-92a-3p | 460 | hsa-miR-191-5p | 192 |
| hsa-miR-27b-3p | 379.5 | hsa-miR-192-5p | 184.5 |
| hsa-miR-200b-3p | 326 | hsa-miR-21-5p | 182 |
| hsa-miR-4485-3p | 301 | hsa-iniR-375 | 177 |
| hsa-miR-30a-3p | 292 | hsa-miR-200c-3p | 164 |
| hsa-miR-501-3p | 286 | hsa-miR-30d-5p | 150.5 |
| hsa-miR-22-3p | 262 | hsa-miR-205-5p | 146 |
| hsa-miR-148a-3p | 239 | hsa-miR-22-3p | 140 |
| hsa-miR-423-3p | 239 | hsa-miR-182-5p | 135 |
| hsa-miR-151a-5p | 227.5 | hsa-miR-125b-5p | 107 |
| hsa-miR-151b | 211.5 | hsa-let-7g-5p | 97 |
| hsa-miR-146b-5p | 209 | hsa-miR-423-3p | 87 |
| hsa-miR-320a | 192 | hsa-miR-937-3p | 76 |

Figure 4B:
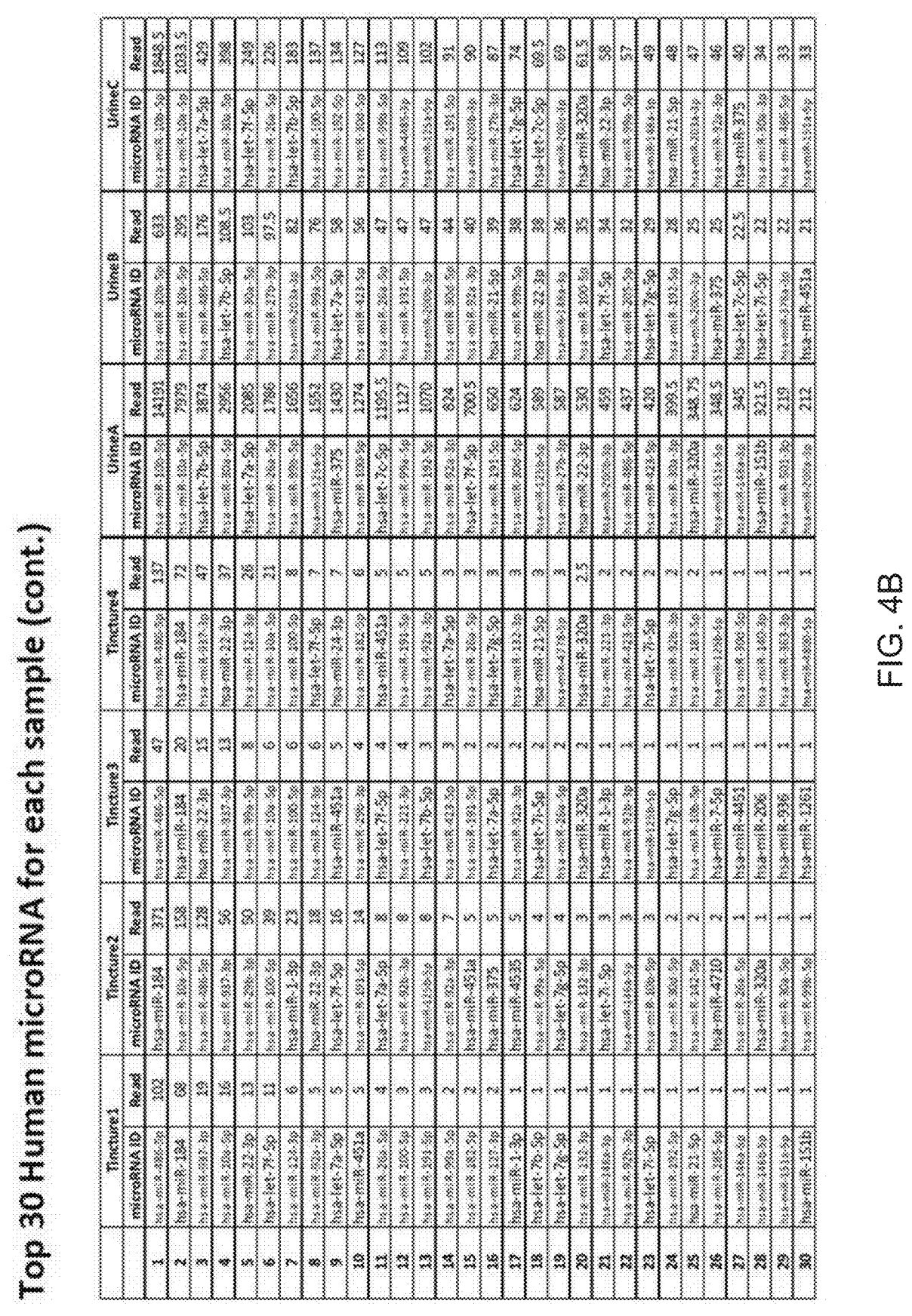

Plant miRNA content can vary depending on the time of year of harvest and mode of extract preparation (i.e. solvent extraction, distillation, maceration, decoction, dried, freeze dried), as well as the mode of administration (i.e. oral tincture/capsule/tablet, sublingual, intranasally, injection, intravenous, topical, etc.). FIGS. 4A-4B and TABLE 5 show the variations in miRNA profiles with fresh plant directly from field versus plant material that is one week old. A 4-day old plant material is represented as "Curcumin", "injection fluid", "oil", "Plant 1", and "Plant 2". Urine A and B show results after use of *Sarracenia* spp. Due to the seasonable variability of plant compounds, miRNA can be standardized synthetically to make medicines.

TABLE 5

Plant microRNA profiles of fresh *Sarracenia flava* (Plant1), fresh *Sarracenia purpurea* (Plant2), fresh *Sarracenia leukophylla* (Plant3), fresh *Sarracenia flava* hybrids (Plant4). Note the profiles of said plants include miRNA that regulate endothelial function, cell division and repair, and p53.

| Plant1 | | Plant2 | | Plant3 | | Plant4 | |
| --- | --- | --- | --- | --- | --- | --- | --- |
| microRNA ID | Read | microRNA ID | Read | microRNA ID | Read | microRNA ID | Read |
| hsa-miR-100-5p | 1181 | hsa-miR-122-5p | 321 | hsa-miR-184 | 83 | hsa-miR-143-3p | 2955 |
| hsa-miR-143-3p | 238 | hsa-miR-143-3p | 213 | hsa-miR-100-5p | 73 | hsa-miR-1-3p | 556 |
| hsa-miR-1-3p | 111 | hsa-miR-100-5p | 148 | hsa-miR-1-3p | 43 | hsa-miR-100-5p | 533 |
| hsa-miR-10b-5p | 78 | hsa-miR-486-5p | 93 | hsa-miR-143-3p | 29 | hsa-miR-486-5p | 384 |
| hsa-miR-486-5p | 57 | hsa-miR-10a-5p | 80 | hsa-miR-937-3p | 26 | hsa-miR-10a-5p | 280 |
| hsa-miR-10a-5p | 54 | hsa-miR-192-5p | 50 | hsa-miR-10b-5p | 20 | hsa-miR-99a-5p | 256 |
| hsa-miR-122-5p | 36 | hsa-miR-10b-5p | 49 | hsa-miR-10a-5p | 14 | hsa-miR-26a-5p | 162 |
| hsa-miR-99b-5p | 27 | hsa-miR-1-3p | 36 | hsa-miR-125b-5p | 9 | hsa-miR-27b-3p | 161 |
| hsa-miR-99a-5p | 26 | hsa-miR-99b-5p | 30 | hsa-miR-486-5p | 7 | hsa-miR-99b-5p | 142 |
| hsa-miR-26a-5p | 21 | hsa-miR-148a-3p | 28 | hsa-miR-22-3p | 7 | hsa-miR-10b-5p | 121 |
| hsa-miR-30a-5p | 19 | hsa-let-7f-5p | 27 | hsa-miR-125a-5p | 6 | hsa-miR-30a-5p | 82 |
| hsa-miR-192-5p | 19 | hsa-miR-99a-5p | 25 | hsa-miR-132-3p | 6 | hsa-miR-191-5p | 783 |
| hsa-miR-148a-3p | 14 | hsa-miR-22-3p | 25 | hsa-miR-99b-5p | 5 | hsa-let-7f-5p | 76 |
| hsa-miR-937-3p | 13 | hsa-miR-26a-5p | 23 | hsa-miR-21-5p | 5 | hsa-miR-378a-3p | 67.5 |
| hsa-let-7f-5p | 12 | hsa-miR-30a-5p | 21 | hsa-miR-181a-5p | 3 | hsa-miR-125b-5p | 67 |
| hsa-miR-30d-5p | 11 | hsa-miR-191-5p | 18 | hsa-miR-24-3p | 3 | hsa-let-7a-5p | 65 |
| hsa-miR-27b-3p | 10 | hsa-let-7a-5p | 18 | hsa-miR-27b-3p | 3 | hsa-miR-30d-5p | 65 |
| hsa-miR-151-5p | 10 | hsa-miR-125b-5p | 17 | hsa-let-7f-5p | 2 | hsa-miR-24-3p | 53 |
| hsa-miR-378a-3p | 10 | hsa-miR-378a-3p | 16 | hsa-miR-99a-5p | 2 | hsa-let-7i-5p | 51 |
| hsa-miR-125b-5p | 9 | hsa-miR-30d-5p | 14 | hsa-miR-146b-5p | 2 | hsa-miR-181a-5p | 46 |
| hsa-miR-92b-3p | 9 | hsa-miR-184 | 14 | hsa-miR-152-3p | 2 | hsa-miR-148a-3p | 45 |
| hsa-let-7a-5p | 8 | hsa-let-7c-5p | 11 | hsa-miR-375 | 2 | hsa-miR-127-3p | 45 |
| hsa-miR-127-3p | 8 | hsa-let-7b-5p | 10 | hsa-miR-151a-3p | 2 | hsa-let-7b-5p | 44 |
| hsa-let-7c-5p | 6 | hsa-miR-21-5p | 10 | hsa-miR-7977 | 2 | hsa-miR-145-5p | 41 |
| hsa-miR-184 | 6 | hsa-miR-146b-5p | 9 | hsa-miR-9-5p | 2 | hsa-let-7g-5p | 40 |
| hsa-miR-125a-5p | 6 | hsa-miR-181a-5p | 9 | hsa-miR-148a-3p | 1 | hsa-miR-126-3p | 35 |
| hsa-let-7b-5p | 5 | hsa-miR-937-3p | 7 | hsa-miR-26a-5p | 1 | hsa-miR-133a-3p | 34 |
| hsa-miR-22-3p | 5 | hsa-miR-125a-5p | 7 | hsa-miR-30a-5p | 1 | hsa-miR-22-3p | 33 |
| hsa-miR-133a-3p | 5 | hsa-miR-133a-3p | 7 | hsa-let-7a-5p | 1 | hsa-miR-30e-5p | 30 |
| hsa-miR-24-3p | 4 | hsa-miR-24-3p | 7 | hsa-miR-378a-3p | 1 | hsa-miR-151a-3p | 28 |

In preferred embodiments, it is at the discretion of the health care provider to identify the medicine right for the patient. Referring to Table 3, for example, if a medicine is desired to help heal inflammation, the injection fluid would be selected. In one embodiment, the injection fluid may be obtained from *S. purpurea* due to its high miRNA-22 content, which would be effective for regulating cytokine function. In another embodiment, if a medicine is needed to heal and repair DNA, an oil infused with *S. flava* and hybrids, such as the Oil in FIG. 4A, may be selected since it would have a high miRNA-486 content.

In some embodiments, the compositions of the present invention may be used in combination with other drugs. For instance, a method for enhancing an efficiency of a drug that is being administered to a subject for treating a disease may comprise co-administering a composition of the present invention with said drug. In some embodiments, a composition, such as Sarravis, may be administered intravenously, intramuscularly, subcutaneously, orally, sublingually, or topically.

As an example, a 57-year old female patient with pre-diabetes and hypercholesterolemia had been taking her prescribed statin for cholesterol, as well as a drug for high-blood pressure, a thyroid medicine, and hormones. The patient was administered one treatment of a Sarravis CT Spine injection with manganese. Referring to TABLE 6, the patient's Hemoglobin A1c and cholesterol decreased to normal levels in less than two months (the first lab was taken one month prior to the treatment) and the patient's pre-diabetes and hypercholesterolemia were resolved. After receiving one treatment of the Sarravis CT Spine formulation, her hemoglobin A1c and total cholesterol levels returned to normal levels.

TABLE 6

| | Pre-Treatment Jul. 14, 2017 | Post Treatment Oct. 11, 2017 | Reference |
| --- | --- | --- | --- |
| Cholesterol | 216 mg/dL Above high normal | 168 mg/dL | 100-199 mg/dL |
| LDL Cholesterol | 124 mg/dL Above high normal | 80 mg/dL | 0-99 mg/dL |
| Hemoglobin A1c | 5.7% Above high normal | 5.3% | 4.8-5.6% |

Without wishing to limit the invention to a particular theory or mechanism, the compositions of the present invention, such as Sarravis, can aid in the upregulation of other medicines. For example, a composition of the present invention may be used in combination with a drug in order to increase an effective intracellular concentration of the drug, or increase bioavailability, or increase tissue penetration of the drug. In some non-limiting embodiments, the present invention may be used in conjunction with cancer drugs, or with drugs for any deleterious condition, including, but not limited to, diabetes or autoimmune diseases, in order to enhance the drugs' efficiency. In other embodiments, the compositions of the present invention, such as Sarravis CT Spine, may be administered by spine injections in conjunction with oral use of the other drugs and/or an injectable of the drug is mixed with Sarravis CT Spine for the spine injections.

According to some embodiments, if medicines, such as any vitamins or minerals, are added to a topical form of a miRNA full-profile plant complex, then the cells would obtain the medicine body-wide. Referring to TABLE 7, this is demonstrated by patient labs that show changes to vitamin and mineral levels, such as zinc, Vitamin C, B$_6$, and magnesium, upon pre- and post-usage of topical administration of a vitamin/mineral oil infusion with plant miRNA.

TABLE 7

Pre lab results and post lab results for a patient topically applying oil containing *Sarracenia* spp. magnesium, vitamin B6, and vitamin C, evidencing the transcellular nature of *Sarracenia* spp. Lower levels of magnesium, vitamin B6, and vitamin C in the post lab results indicate that the magnesium, vitamin B6, and vitamin C were being uptaken and used by the cells, as opposed to the pre lab results.

|  | Pre lab results Jul. 6, 2016 | Post lab results Jul. 12, 2016 | Reference |
|---|---|---|---|
| Magnesium | 5.2 mg/dL | 4.2 mg/dL | 4.0-6.4 mg/dL |
| Vitamin C | 1.2 mg/dL | 1.0 mg/dL | 0.2-1.5 mg/dL |
| Zinc | 112 | 80 mcg/dL | 60-130 mcg/dL |
| Vitamin B6 | 46.8 ng/mL | 19.2 ng/mL | 2.1-21.7 ng/mL |

Without wishing to limit the invention to a particular theory or mechanism, it is theorized that the key for achieving healing and homeostasis is to use the miRNA plant profile medicine that the patient is missing. Referring to FIG. 4B, if the patient is missing miRNA-486, then Tincture 4 having miRNA-486 could be used to introduce this missing miRNA, thereby inducing changes in the patient's health. The patient's pre- and post miRNA profile show the introduction of miRNA, where the *Sarracenia* spp. has increased miRNA-486.

In an alternative embodiment, a miRNA profile of meat, such as beef, may be used to prepare a medicine for patients who are anemic. miRNA formulations are unlimited and may be synergized with other components, such as vitamins, minerals, and plant extracts, to bring about further synergistic effects. In one embodiment, for example, *Rosa damascena* and related species may be added to a baseline miRNA formula that focuses on DNA repair.

In other embodiments, the miRNA profile of bacteria may be mapped to human miRNA. By mapping the bacteria to human miRNA, the miRNAs of bacteria are matched to human microRNAs, thus generating a bacteria microRNA profile. Thus, in some embodiments, the present invention also provides a method of microRNA profiling a bacteria to human microRNAs. The method may comprise obtaining a sample of the bacteria, and mapping microRNAs in said bacteria sample to human microRNAs to identify target microRNAs of the bacteria sample that appear in the human microRNAs, thus generating a bacteria microRNA profile comprising the target microRNAs. The step of mapping the microRNAs may comprise assaying bacteria sample and matching the bacteria miRNAs to human miRNAs to identify the human miRNA content in said bacteria sample.

Figure 8:
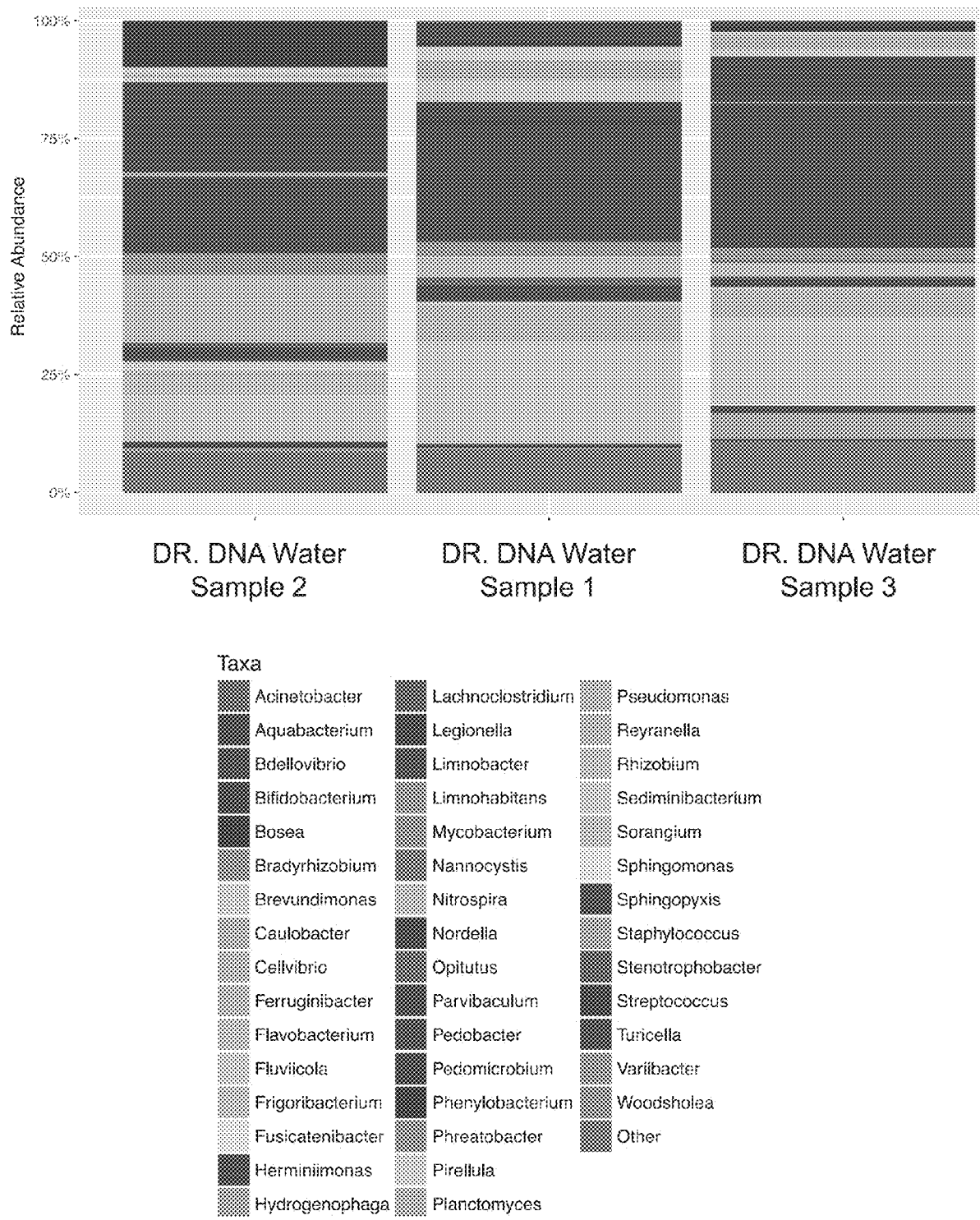
FIG. 8 shows the identified taxa at the genus level (top 45 genera shown).

In some embodiments, the bacteria sample may be obtained from a culture of the bacteria. Referring to FIG. 8, non-limiting examples of bacteria genera that can be mapped to human miRNA include *Acinetobacter, Aquabacterium, Bdellovibrio, Bifidobacterium, Bosea, Bradyrhizobium, Brevundimonas, Caulobacter, Cellvibrio, Ferruginibacter, Flavobacterium, Fluviicola, Frigoribacterium, Fusicatenibacter, Herminiimonas, Hydrogenophaga, Lachnoclostridium, Legionella, Limnobacter, Limnohabitans, Mycobaterium, Nannocystis, Nitrospira, Nordella, Opitutus, Parvibaculum, Pedobacter, Pedomicrobium, Phenylobacterium, Phreatobacter, Pirellula, Planctomyces, Pseudomonas, Reyranella, Rhizobium, Sediminibacterium, Sorangium, Sphingomonas, Sphingopyxis, Staphylococcus, Stenotrophobacter, Streptococcus, Turicella, Variibacter, Woodsholea*, and others. In some embodiments, the bacteria may be swamp and bog bacteria.

In some embodiments, the bacteria microRNA profile may comprise levels of target microRNAs. The target microRNAs can be hsa-let-7, miR-10, hsa-miR-22-3p, miR-100-5p, miR-101, miR-125a-5p, miR-148a-3p, miR-182-5p, miR-191-5p, miR-192-5p, miR-200-c, miR-26a-5p, miR-27b-3p, miR-30, miR-375, miR-378a-3p, miR-4485-3p, miR-486-5p, miR-937-3p, miR-92a-3p, and miR-99. Without wishing to limit the invention, the target microRNAs may be effective for modulating DNA damage repair, endothelial, and mitochondrial function. In some embodiments, the method may further comprise isolating and extracting one or more of the target microRNAs from the bacteria sample. In some embodiments, the target microRNAs can be prepared into a medicament that promotes DNA damage repair.

TABLE 8

Bacteria microRNA profiles of bacteria found in DR. DNA water samples and distilled water sample. Without wishing to limit the present invention to a particular theory or mechanism, it is believed that the microRNA originated from bacteria in the water samples.

|  | DR. DNA Water in glass (Chilled) G32 | Distilled Water G33 | Dr. DNA Water in plastic (at Room temperature) G34 |
|---|---|---|---|
| hsa-let-7 Total | 170,430,478 | 198,672,108,512 | 608,914,285,714 |
| hsa-miR-10a Total | 0 | 0 | 119,235,714,286 |
| hsa-miR-10b Total | 995,947 | 19,789,866,837 | 117,935,714,286 |
| hsa-miR-26a-5p | 121,443,457 | 86,025,352,867 | 127,735,714,286 |
| hsa-miR-27b-3p | 279,003,798 | 570,740,052,547 | 82,535,714,286 |
| hsa-miR-30 Total | 48,046,532 | 11,685,843,753 | 230,871,428,571 |
| hsa-miR-92a-3p | 46,985,411 | N/A | 95,535,714,286 |
| hsa-miR-99 Total | 14,562,044 | 0 | 98,335,714,286 |
| hsa-miR-100-5p | 369,627 | N/A | 92,235,714,286 |
| hsa-miR-101 Total | 10,877, 818 | 0 | 96,135,714,286 |
| hsa-miR-125a-5p | 1,209,274 | N/A | N/A |
| hsa-miR-148a-3p | 33,921,803 | N/A | N/A |
| hsa-miR-182-5p | N/A | N/A | N/A |
| hsa-miR-191-5p | 1,488,791 | N/A | 120,835,714,286 |
| hsa-miR-192-5p | 4,269,718 | N/A | 69,335,714,286 |
| hsa-miR-200 Total | 46,018,465 | 0 | 93,735,714,286 |
| hsa-miR-375 | N/A | N/A | N/A |
| hsa-miR-378a-3p | N/A | N/A | 87,335,714,286 |
| hsa-miR-486-5p | 699,376 | N/A | 77,235,714,286 |
| hsa-miR-4485 | 70,724,636 | 454,044,534,541 | 39,535,714,286 |

Case Studies

The following are non-limiting examples of patients that were treated using the compositions and methods of the present invention. These examples are presented for illustrative purposes only, and are in no way intended to limit the present invention. Equivalents or substitutes are within the scope of the invention.

Example 1: Hashimoto's Disease

A patient suffering from Hashimoto's disease was resolved upon use of a *Sarracenia* hybrid tincture (Tincture 4 of FIG. 4B), which contained high levels of miR-486. Hashimoto's disease is a condition in which the immune system attacks the thyroid gland. Elevated Anti-TPO (32 IU/mL) and TSH (24.660 uIU/mL) in the pre lab results were significantly reduced to 18 IU/mL and 2.240 uIU/mL, respectively, in the post lab results.

Example 2: Inflammation

A 27-year old female patient has been experiencing pain in her big toe for about a year. The patient received a spine injection of a Sarravis CT Spine composition. She experienced pain in her left foot, which went away, and she no longer has pain her foot. She was able to hike and run after the treatment.

Example 3: Stress

A 37-year old female patient was experiencing stress from work. Her doctor had diagnosed her with oligodendroglioma and zinc dependency. The doctor administered an injection of 15 cc of a Sarravis CT Spine formula near the du14-4, and a Sarravis IV to her right lateral hand vein for over 5 minutes. The Sarravis IV formulation contained 3 cc of normal saline, 1 cc of Sarapin®, 1 cc of 2.5 mg/ml zinc, 1 cc of 1 mg/ml selenium, 1 cc of 500 mg/ml magnesium, 1 cc of 100 mg/ml NAC, 1 cc of 2 mg/ml manganese, and 1 cc of 200 mg/ml glutathione.

Example 4: Peripheral Neuropathy

A 56-year old male patient had peripheral neuropathy caused by interferon injections that he received years ago. His doctor administered a spinal injection of 15 cc (5 of 3 cc syringes) of the Sarravis CT Spine. He further received 4 more rounds of the Sarravis CT Spine injection treatment. After completion of the treatments, the neuropathy was gone.

Example 5: Miscarriage

A 35-year old patient had tried for three years to get pregnant, but resulted in three miscarriages early in the pregnancy. Her doctor recommended that she decrease her sugar intake, wine intake, and prescribed that she drink water with the rate limiters (DR. DNA water). The patient was also administered an IV composition of 250 cc normal saline, 2 cc of 500 mg/ml magnesium sulfate, 1 cc of 1 mg/ml selenium, 1 cc of 100 mg/ml NAC, 1 cc of 2 mg/ml manganese, 1 cc of 2.5 mg/ml zinc, 5 cc of 200 mg/ml glutathione, 1.5 cc 1000 cyano, and 0.5 cc of B-100 complex. The water and IV reduced inflammation and provided zinc, which is needed to spark conception. The patient became pregnant two weeks later and is still pregnant. The patient is continuing to drink the DR. DNA water.

Example 6: Deep-Vein Thrombosis

A female patient presented to her doctor a long history of Lyme's diseases, iron deficiency anemia, deep-vein thrombosis (clot) to the left (popliteal/femoral), fatigue, shortness of breath, chronic pain, insomnia, autoimmune thyroditis, abdominal pain, seizures, and tachycardia. After performing preliminary treatments, her doctor had concluded that she had two underlying primary conditions: iron deficiency anemia and anti-phospholipid syndrome. The patient had become a vegetarian 20 years ago, and her health had declined since then. Her doctor further concluded that she was low in all rate limiters, particularly cysteine and zinc. Thyroid labs, other than antibodies, tended to be normal. She had elevations in anti-tpo, anti-phospholipids, and G6PD. Her miRNA profile showed a very high level of endothelial activity, such as elevations in miR-10, which regulates epithelial to mesenchymal transition (EMT). Her doctor administered spine injections of Sarravis CT Spine with zinc at a high dose (9 cc of 2.5 mg/ml). The clot was resolved and the patient was became committed to consuming foods high in zinc. The patient further received IV infusion treatments of iron and her anemia resolved, as did 90% of her symptoms, including the seizures and polyarthralgia.

Example 7: Brain Tumor

An MRI brain scan with and without contrast of a patient that had a brain tumor (oligoastrocytoma) was ordered on Mar. 15, 2017. Prior to receiving treatment with the present invention, the brain tumor had re-occurred twice in the patient. After receiving treatments, the results showed no more existence of metastatic disease. Impression: 1. Stable resection cavity. No convincing evidence of tumor progression/recurrence. 2. No evidence of acute intracranial hemorrhage or infarction. 3. Volume loss. No hydroencephalus. 4. Improved aeration of the paranasal sinuses, particularly the left maxillary sinus.

Example 8: Neuroma

A patient's neuroma was aggravated via swimming in a pool and hours of dancing. Swelled, very painful a few days ago. Injection was tried but the pain was too much. It is likely the spine miRNA is needed to get the systemic profile lower. Spinal injection of 15 cc CT was administered from T12-L5 supraspinous 30 g 1 inch of 5 syringes with 1.0 cc miRNA 486, 0.5 cc sarapin, 0.5 cc miR 100, 1 cc glutathione 200 mg/ml in each syringe. Next day, body tingling started after the injection, so a push into the L hand vein lateral of 1 cc each Rate Limiter. Then the lesion really started to heal within an hour. Also applying every 1-2 hours cytenssic lotion. Patient reported the lesion was almost gone and pain is no more.

Example 9: Liver Cancer

TABLE 9

Tracking a history of a patient with liver cancer. Progression of the liver cancer ceased after receiving Sarravis CT Spine injections.

| Date of Exam | Impression |
| --- | --- |
| Jul. 11, 2016 | Numerous liver masses increased in size since the prior examination. Negative for cholelithiasis. |
| Oct. 21, 2016 | Large masses in the liver similar to the previous study. No new abnormality. |
| Feb. 1, 2017 | Stable large hepatic masses consistent with the provided history of cancer. No new findings. |

Example 10

A patient was administered a composition of miRNA-486 and zinc 2x/week. Hemoglobin A1c Reference: 4.8-5.6%. Pre-diabetes: Hemoglobin A1c=5.7-6.4%. Pre lab result: Hemoglobin A1c=6.0%, above high normal. Post lab result: Hemoglobin A1c=5.7%.

Example 11

Female Patient was Administered Spine Injections of Sarravis CT Spine. Hemoglobin A1c Reference: 4.8-5.6%. Pre-diabetes: Hemoglobin A1c=5.7-6.4%. Pre lab result May 17, 2017: Hemoglobin A1c=6.0%, above high normal. Post lab result Jul. 20, 2017: Hemoglobin A1c=5.7%. Post lab result Sep. 11, 2017: Hemoglobin A1c=5.6%. Note that Hemoglobin A1c decreased to normal levels within 4 months, which usually does not heal quickly and would normally take months to years with diet changes alone.

Example 12

TABLE 10A shows pre lab results and TABLE 9B-9C show post lab progression results for another patient with diabetes and *E. coli* who was administered spine injections of Sarravis CT Spine.

TABLE 10A

Pre Lab Results collected Jul, 19, 2017.
Values Outside of Reference Range

| TEST | RESULTS | REFERENCE RANGES | UNITS |
|---|---|---|---|
| Immature Granulocytes | 1.7 H | 0.0-1.0 | % |
| Glucose | 288 H | 65-99 | mg/dL |
| Globulin | 4.1 H | 2.0-3.7 | g/dL |
| Albumin/Globulin Ratio | 0.8 L | 1.0-2.4 | |
| Aspartate Aminotransferase | 9 L | 10-41 | IU/L |
| Triglyceride | 2.59 H | ≤149 | mg/dL |
| Cholesterol/HDL Ratio | 6.7 H | ≤4.4 | |
| HDL Cholesterol | 27 L | ≥46 | mg/dL |
| VLDL Cholesterol | 52 H | ≤29 | mg/dL |
| Phosphorus (Inorganic) | 2.4 L | 2.5-4.5 | mg/dL |
| Hemoglobin A1c | 12.0 H | ≤5.6 | % |
| Clarity, Urine | Slightly Cloudy | Clear | |
| Blood, Urine Qualitative | Small | Negative | |
| Glucose, Urine Qualitative | 500 H | Negative | mg/dL |
| Protein, Urine Qualitative | Trace | Negative | mg/dL |
| Culture, Urine | | | |

Mixed Gram positive and Gram negative flora 10,000-50,000 CFU/mL

TABLE 10B

Post Lab Results collected Aug. 8, 2017.
Values Outside of Reference Range

| TEST | RESULTS | REFERENCE RANGES | UNITS |
|---|---|---|---|
| Glucose | 161 H | 65-99 | mg/dL |
| Hemoglobin A1c | 10.5 H | ≤5.6 | % |
| Specific Gravity, Urine | 1.002 L | 1.005-1.030 | |

TABLE 10C

Post Lab Results collected Sep. 1, 2017.
Values Outside of Reference Range

| TEST | RESULTS | REFERENCE RANGES | UNITS |
|---|---|---|---|
| Glucose | 209 H | 65-99 | mg/dL |
| Hemoglobin A1c | 9.7 H | 5.56 | % |

Example 13: Autoimmune Disease

A patient had an autoimmune disease. The patient was prescribed a treatment of 3 tsp/day of a *Sarracenia flava* and hybrid oral tincture. After 10 months of treatment, the post lab results showed that the patient had healed from the autoimmune disease, as shown in TABLE 11.

TABLE 11

Pre lab results and post lab results.

| | Pre lab results Aug. 27-28, 2015 | Post lab results Jun. 9, 2016 | Reference |
|---|---|---|---|
| ANA | Positive Abnormal | Negative | Negative |
| Anti-DNA | 35 EU Above high normal | <1 IU/mL | 0-19 EU |
| RNP Antibodies | 2.4 AI Above high normal | 2.0 AI Above high normal | 0.0-0.9 AI |

Example 14

A patient was drinking a water product with the rate limiters magnesium, selenium, and zinc (DR. DNA water) of the present invention. The patient was previously drinking distilled water when the patient's red blood count (RBC) was below normal levels, as shown in TABLE 12. Note the change in the RBC that increased back to normal levels after drinking the water with rate limiters. The symptom that went away was chronic bouts of pericarditis.

TABLE 12

RBC Procedure

Procedure

RBC
Reference Range

[4.70-6.00]
Units $\times 10^{\wedge}6/\text{uL}$

| Collected Date/Time | |
|---|---|
| Jul. 7, 2017 07:53 MST | 5.05 |
| May 11, 2017 07:00 MST | 5.25 |
| Mar. 24, 2017 07:54 MST | 5.03 |
| Jun. 3, 2016 06:40 MST | 5.55 |
| May 26, 2016 04:00 MST | $4.56^L$ |
| May 25, 2016 03:00 MST | $4.10^L$ |
| May 24, 2016 00:45 MST | $4.01^L$ |
| May 23, 2016 01:15 MST | $4.41^L$ |
| May 22, 2016 06:35 MST | $4.69^L$ |
| May 14, 2016 00:25 MST | 5.48 |

Example 15

An 80-year old female patient complained about pain. On May 24, 2017, she woke around 4 in the morning with "a kind of pain I have never had at my liver and so intense it was awful". She tried to use the restroom but "only a little stool came out and a little urine". She was administered an IV composition comprising miRNA and rate limiters, which lowered her blood pressure (BP) to normal levels quickly. IV composition: 20 cc push to R antec. 23 g ¾ butterfly used of 5 cc normal saline/10 cc sarapin/100 mg NAC/1 cc Se 1 mg/1 cc mag sulfate 500 mg/1 cc Mn 2 mg/1 cc glutathione 200 mg/1 cc zinc 2.5 mg. BP pre tx L sitting 160/80; BP pre tx R sitting 180/90; murphy's negative; BP R post TX sitting 120/60.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A method of preparing an injectable medicine for treating cancer, a tumor, or a clot in a subject, said method comprising:
   combining therapeutic amounts of at least 0.001 nmol/ml of miR-486, and at least 0.001 mg/ml of glutathione, in sterile water to produce the injectable medicine;
   wherein the medicine is effective for promoting healing and DNA damage repair when injected into the subject, thereby treating the cancer, tumor, or clot.

2. The method of claim 1 further comprising adding vitamins, minerals, amino acids, or a combination thereof to the injectable medicine.

3. The method of claim 1 further comprising adding selenium, zinc, cysteine, manganese, miR-708, or a combination thereof to the injectable medicine.

4. The method of claim 1, wherein the medicine is administered by subcutaneous or intramuscular injection near or above a spine of the subject.

5. A composition for repairing DNA damage comprising:
   a. an extract comprising at least 0.001 nmol/ml of miR-486; and
   b. at least 0.001 ma/ml of glutathione.

6. The composition of claim 5, further comprising vitamins, minerals, amino acids, or a combination thereof.

7. The composition of claim 5 further comprising selenium, zinc, cysteine, manganese, miR-708, or a combination thereof.

8. The composition of claim 5, wherein the composition is formulated for subcutaneous or intramuscular injection near or above a spine.

9. The composition of claim 5, wherein the extract comprising miR-486 is extracted from a pitcher plant.

10. The composition of claim 5 further comprising a plant preparation obtained from a carnivorous plant.

11. The composition of claim 10, wherein the carnivorous plant is *Sarracenia flava, Sarracenia purpurea, Sarracenia leukophyll*, or hybrids thereof.

* * * * *